(12) United States Patent
Sendai et al.

(10) Patent No.: US 6,468,204 B2
(45) Date of Patent: Oct. 22, 2002

(54) FLUORESCENT ENDOSCOPE APPARATUS

(75) Inventors: Tomonari Sendai, Kaisei-machi (JP); Kazuo Hakamata, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/864,326

(22) Filed: May 25, 2001

(65) Prior Publication Data

US 2002/0013512 A1 Jan. 31, 2002

(30) Foreign Application Priority Data

May 25, 2000 (JP) ........................................ 2000-154996
Jul. 14, 2000 (JP) ........................................ 2000-214727

(51) Int. Cl.$^7$ ................................................. A61B 1/06
(52) U.S. Cl. ...................... 600/160; 600/108; 600/118; 600/178; 606/12
(58) Field of Search ................................ 600/108, 109, 600/117, 118, 160, 178, 180, 476, 478; 606/11, 12, 14–16; 607/89

(56) References Cited

U.S. PATENT DOCUMENTS 4,993,404 A * 2/1991 Lane .......................... 348/705
5,419,312 A * 5/1995 Arenberg et al. ........... 600/108
6,066,129 A * 5/2000 Larson ......................... 606/10

* cited by examiner

Primary Examiner—John Mulcahy
(74) Attorney, Agent, or Firm—Sughrue Mion, PLLC

(57) ABSTRACT

According to a fluorescent endoscope apparatus for detecting an autofluorescent-light image emitted from a living body upon irradiation thereof by stimulating light, when the endoscope insertion portion is inserted into or removed from a patients body, stimulating light is prevented from entering the eyes of the patient or the operator, ensuring for their safety. When the endoscope insertion portion is outside the body of a patient, the flicker occurring due to the fluorescent or other light illuminating the diagnosis room, which would be detected together with the autofluorescent-light image by a fluorescent-image use camera or with the normal image by a normal-image use camera, is detected by a flicker detector. The flicker detector outputs a detection signal to the stimulating light emission prevention controller, which turns off the power source to the stimulating light laser source by use of a controller computer and thereby prevents the emission of stimulating light.

25 Claims, 17 Drawing Sheets

RGB HISTOGRAM OF THE BACKGROUND LIGHT OF THE DIAGNOSIS ROOM

RGB HISTOGRAM OF A BODY CAVITY

```
0 0 0      0 1 0      0 0 1
1 1 1      0 1 0      0 1 0
0 0 0      0 1 0      1 0 0
```

F I G. 12
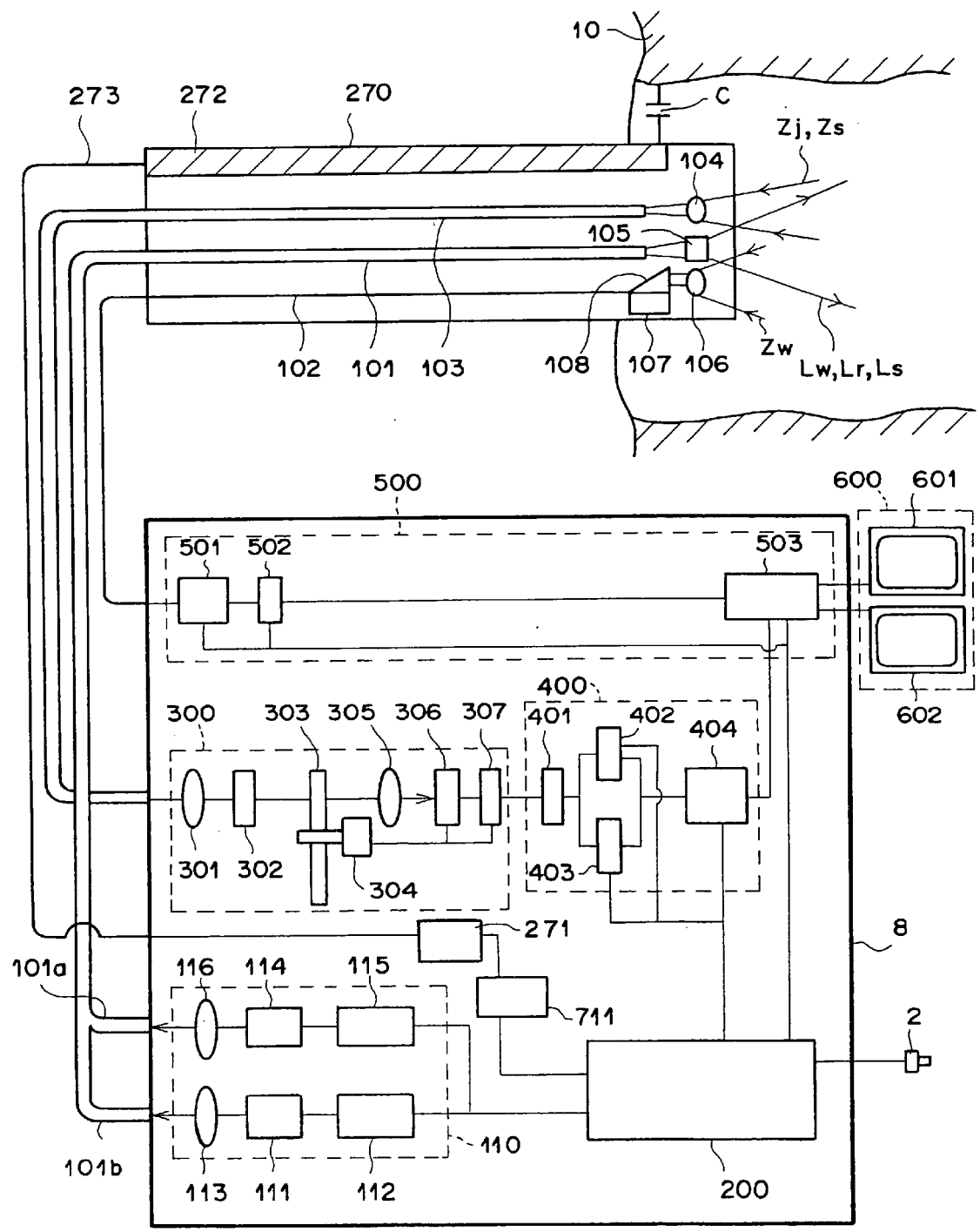

F I G . 16
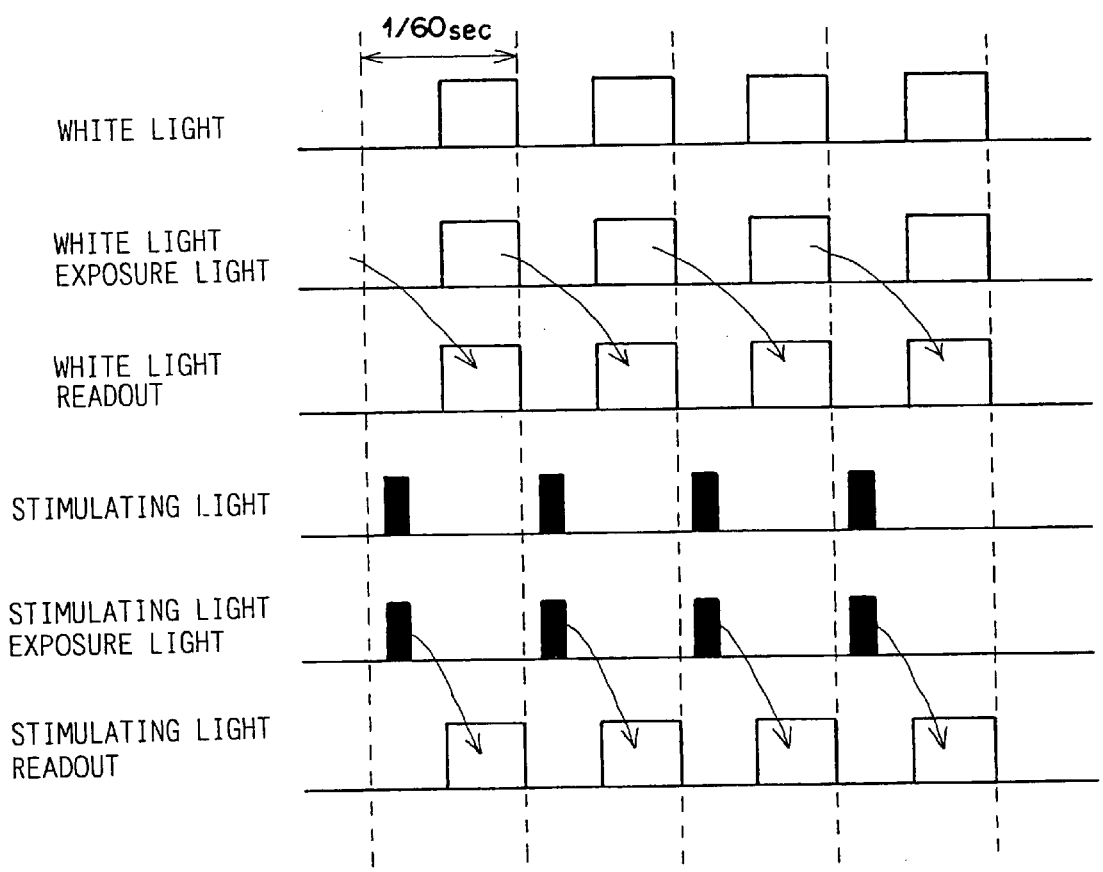

FLUORESCENT ENDOSCOPE APPARATUS

BACKGROUND OF THE INVENTION

1. Field of the Invention

The present invention relates in general to a fluorescent endoscope apparatus, and in particular to a fluorescent endoscope apparatus for insertion into the body of a living subject, irradiating a living-tissue subject with stimulating light, measuring the fluorescent light emitted by the living-tissue subject upon irradiation thereof by the stimulating light and detecting a fluorescent image formed of the emitted fluorescent light.

2. Description of the Related Art

There have been proposed technologies for irradiating a living-tissue subject with stimulating light, receiving the fluorescent light emitted from the living-tissue subject thereupon, wherein, utilizing the difference between the fluorescent light emitted from a normal tissue and the fluorescent light emitted by a diseased tissue upon irradiation thereof by a stimulating light of a predetermined wavelength, a fluorescent image of the location of the diseased tissue and it's range of infiltration is displayed.

Normally, when irradiated by stimulating light, as shown by the solid line in FIG. 18, because a strong fluorescent light is emitted by normal tissue and a weaker fluorescent light is emitted from diseased tissue, as shown by the broken line in the same figure, by measuring the strength of the fluorescent light, it can be determined whether the living-tissue subject is in a normal state or a diseased state.

Further, when the strength,of the fluorescent light emitted due to irradiation by stimulating light is displayed as an image, because there is unevenness in the living-tissue subject, the strength of the stimulating light projected onto the living-tissue subject is not uniform. In addition, although the strength of the fluorescent light emitted from the living-tissue subject is substantially proportionate to the strength of stimulating light, the strength of the stimulated light is in inverse proportion to the square of the distance. Therefore, there, are cases in which the fluorescent light emitted from a diseased tissue closer to the light source than a normal tissue is received as the fluorescence of higher strength, and therefore, it is not possible to discern with certainty the state of the irradiated tissue based solely on the strength of received fluorescent light emitted due to irradiation by stimulating light. In order to reduce this uncertainty, a method in which the ratio of the two different strengths of fluorescent light is obtained by division, and a method of displaying a computed image based on the value of the resultant of the division operation, that is, for example, an image display method taking into account the difference of the form of the spectra of the fluorescent light reflecting the characteristics of the living tissue, or a method of irradiating a living-tissue subject with a near-infrared light which is absorbed uniformly by various living-tissues as a reference light, detecting the strength of the reflected light of the reference light reflected by a living-tissue subject upon irradiation thereof by the reference light, obtaining by division the ratio thereof to the strength of the fluorescent light, and displaying a computed image based on the value of the resultant of the division operation, that is, a method of obtaining the value reflecting the rate of fluorescent light absorption and displaying an image, has been proposed.

In addition, using the technology described above, the development of a fluorescent endoscope apparatus for detecting a fluorescent image of the inside of a living body is advancing. Because the strength of the fluorescent light detected by such fluorescent endoscope apparatuses is extremely weak, it is desirable that the stimulating light be of as high strength as possible. However, because laser light is used as the source of stimulating light, the safety of the patient to be subjected to diagnosis and the operator must be ensured for. Values of the density of laser light to be used as stimulating light are defined as MPE values according to the JIS standard, etc. Up to now, when the endoscope insertion portion of a fluorescent endoscope apparatus has been inserted into a body cavity of a patient, because the output face of the stimulating light projecting end portion of the endoscope insertion portion comes to be in extremely close proximity to a target area, the target area is irradiated by the energy of laser light of too high an energy density, and because there is a fear that injury be caused to the patient, a safety device for the prevention thereof has been proposed.

However, for cases in which stimulating light is emitted when inserting the endoscope insertion portion of a fluorescent endoscope apparatus into or removing the endoscope insertion portion from the body cavity of a patient, there is a fear that injury be caused to the eyes of the patient or the operator, and up till now, a safety device for the prevention thereof has not been proposed.

In addition, when starting;the system, resetting the system, starting the measurement procedure, or performing maintenance on the system, it is considered possible that stimulating light be inadvertently projected at areas other that the section of which a measurement is to be taken. Here: starting the system refers to turning on the fluorescent endoscope apparatus; resetting the system refers to returning controlling characteristics of the fluorescent endoscope apparatus to the initial state after it has already been turned on; starting the measurement procedure refers to an operator's preparing to take a measurement, after the fluorescent endoscope apparatus has been turned on, of the section of which a measurement is to be taken; performing maintenance on the system refers to the preparations that must be made when a maintenance operation requiring that stimulating light be emitted is to be performed.

Also, safety measures for times when starting the system, resetting the system, initiating operations to take a measurement, or performing maintenance on the system, as described above, against inadvertent emission of stimulating light have also not been proposed.

SUMMARY OF THE INVENTION

The present invention has been developed in consideration of the circumstances described above. It is a primary objective of the present invention to provide a fluorescent endoscope apparatus having a safety device for preventing injury to the eyes or other body parts of the patient and operator due to the inadvertent emission of stimulating light when starting the system, resetting the system, initiating measurement, performing maintenance requiring the emission of stimulating light, etc.

The first fluorescent endoscope apparatus according to the present invention comprises a projecting means for emitting stimulating light and illuminating light, an endoscope insertion portion for insertion into the body of a patient, a light guiding means provided within said endoscope insertion portion for guiding the stimulating light and illuminating light emitted from the projecting means to the section of which a measurement is to be taken, and detecting means for detecting a fluorescent image formed of the fluorescent light emitted from the section of which a measurement is to be taken upon irradiation thereof by stimulating light guided through the guiding means and a normal image of the light reflected from the section of which a measurement is to be taken upon irradiation thereof by the illuminating light guided through the guiding means, further comprising a stimulating light emission preventing means for preventing the emission of the stimulating light, a detecting means for detecting that the forward end portion of the insertion portion is outside of the body of the patient, and a stimulating light emission prevention controlling means for preventing, via the stimulating light emission preventing means, the emission of stimulating light, based on the detection signal detected by the:detecting means.

In addition, the detecting means of the second fluorescent endoscope apparatus according to the present invention is provided with a flicker detecting means for detecting the flicker appearing due to the light illuminating the inside of the diagnosis room, which is different from the stimulating light emitted by the projecting means, and a stimulating light emission prevention controlling means for preventing, via the stimulating light emission preventing means, the emission of stimulating light, based on the detection signal detected by the flicker detecting means.

Here, "flicker" refers to periodical change in brightness occurring in the diagnostic room illumination (diagnostic room illumination refers to light, such as that a from fluorescent bulb, of which the quantity changes a cycles twice that of an off-the-shelf electric power source) that is detected by the fluorescent endoscope apparatus when a measurement operation is carried out. The flicker detecting means can be a means for detecting the flicker appearing in a normal image or a fluorescent image detected by the image detecting means, or a means for detecting only the flicker occurring at the end portion of the endoscope insertion portion. In the latter case, it is desirable that the flicker detecting means is disposed at a position several centimeters from the stimulating light projecting end:,portion of the endoscope insertion portion. Note that for cases in which the flicker appearing in a normal or fluorescent image is to be detected, flicker occurs when the normal or fluorescent image detecting cycle and the frequency of an of-the-shelf electric power source differ, and because flicker does not occur when the image detecting cycle and the frequency of the of-the-shelf electric power source are equivalent or when one the frequency of either of the two is an integer. multiple of the other, it is necessary to take the image detecting cycle into consideration. When flicker is present, the flicker detecting means outputs a detection signal assuming that the end portion of the endoscope insertion portion is located outside the body of the patient. Note that the expression "outside the body of the patient" refers to positions at which there is a fear that the stimulating light emitted from the end portion of the endoscope insertion apparatus enter the eyes of the patient or the operator, or positions at a predetermined safe distance from positions where the potential for the stimulating light to inadvertently be projected into the eyes of the patient or operator.

In addition, the detecting means of the third fluorescent endoscope apparatus according to. the present invention is provided with a brightness distribution detecting means for detecting the difference between the brightness distribution of the brightness distribution of the normal image and the brightness distribution occurring within the body of a patient, and a stimulating light emission prevention controlling means for preventing, via the stimulating light emission preventing means, the emission of stimulating light, based on the detection signal detected by the brightness distribution detecting means.

Here, for cases in which the subject of a measurement to be obtained by use of a fluorescent endoscope apparatus is, for example, the tube-shaped organs (the esophagus, the stomach, the duodenum, the large intestine, etc.), the brightness distribution occurring in a normal image of the inside of the body of a patient is brighter on the circumference of the image than in the middle of the image, and because it differs with the brightness distribution of a normal image taken outside of the body of the patient, it can be determined from the state of the brightness distribution of a normal image whether the end portion of the endoscope insertion portion is inside or outside the body of the patient. When the detected brightness distribution state differs from the brightness distribution when the forward end portion of the endoscope insertion portion is inside the body of the patient, the brightness distribution detecting, means outputs a detection signal assuming that the end portion of the endoscope insertion portion is located outside the body of the patient.

In addition, the detecting means of the fourth fluorescent endoscope apparatus according to the present invention is provided with a brightness detecting means for detecting that the brightness of a normal image differs from the brightness measured when the forward end portion of the endoscope insertion portion is inside the body of the patient, and a stimulating light emission prevention controlling means for preventing, via the stimulating light emission preventing means, the emission of stimulating light, based on the detection signal detected by the brightness detecting means.

Here, when the brightness of any of the pixels of a normal image is above a predetermined threshold value, the brightness detecting means recognizes the end portion of the endoscope insertion portion as being outside the body of the patient and outputs a detection signal.

In addition, the detecting means of the fifth fluorescent endoscope apparatus according to the present invention is provided with a color signal detecting means for detecting that the color signal of a normal image differs from the color signal occurring when the forward end portion of the endoscope insertion portion is inside the body of the patient, and a stimulating light emission prevention controlling means for preventing, via the stimulating light emission preventing means, the emission of stimulating light, based on the detection signal detected by the color signal detecting means.

Here, for cases in which the color signal, which is an RGB color signal, of any of a normal image detected by the fluorescent endoscope apparatus is of a normal image of the inside of the body of a patient, because it is an image of mucous membranes and blood vessels, the R signal is large in comparison to the G and B signals. Accordingly, when the value of the R signal is smaller than a predetermined threshold value, the color signal detecting means recognizes the end portion of the endoscope insertion portion as being outside the body of the patient and outputs a detection signal.

In addition, the detecting means of the sixth fluorescent endoscope apparatus according to the present invention is provided with a straight-line detecting means for detecting that the straight-line pattern of a normal image differs from the straight-line pattern occurring when the forward end portion of the endoscope insertion portion is inside the body of the patient, and a stimulating light emission prevention controlling means for preventing, via the stimulating light emission preventing means, the emission of stimulating light, based on the detection signal detected by the straight-line detecting means.

Here, because a normal image detected by the fluorescent endoscope apparatus when the end:portion of the endoscope insertion portion is outside of the patients body is a normal image of the of the environment of the diagnosis room, there are more straight-line patterns contained therein than in a normal image of the inside of the body of the patient. When the number of lines within a normal image is above a predetermined threshold value, the straight-line detecting means recognizes the end portion of the endoscope insertion portion as being outside the body of the patient and outputs a detection signal. Note that as straight-line detecting method, there is a method employing image processing by a Hough transform and detecting the straight lines, or a method wherein an image template consisting of only straight lines is superposed on a normal image and the straight-line component of the normal image is thereby enhanced, and the straight lines detected, etc.; in short, any method of detecting the straight-line component occurring in a normal image can be employed.

In addition, the detecting means of the seventh fluorescent endoscope apparatus according to the present invention is provided with a light strength detecting means disposed in the end portion of the endoscope insertion portion for detecting that the light strength occurring near the side of the end portion of the endoscope insertion portion differs from the light strength inside the body of the patient, and a stimulating light emission prevention controlling means for preventing, via the stimulating light emission preventing means, the emission of stimulating light, based on the detection signal detected by the light strength detecting means.

Here, because the brightness of the area near the side of the end portion of the endoscope insertion portion of the endoscope apparatus is brighter when the end portion of the endoscope insertion portion is outside of the body of the patient than when it is inside the body of the patient, when the detected light strength is above a predetermined threshold value, the light strength detecting means recognizes the end portion of thee endoscope insertion portion as being outside of the body of the patient and outputs a detection signal. Further, it is desirable that the light strength detecting means be disposed at a safe position at a distance several centimeters from the stimulating light emitting end portion of the endoscope insertion portion.

In addition, the detecting means of the eighth fluorescent endoscope apparatus according to the present invention is provided with a temperature detecting means disposed in the end portion of the endoscope insertion portion for detecting that the temperature occurring near the side of the end portion of the endoscope insertion portion differs from the temperature inside the body of the patient, and a stimulating light emission prevention controlling means for preventing, via the stimulating light emission preventing means, the emission of stimulating light, based on the detection signal detected by the temperature detecting means.

Here, because the temperature of the area near the side of the end portion of the endoscope insertion portion of the endoscope apparatus is lower when the end portion of the endoscope insertion portion is outside of the body of the patient than when it is inside the body of the patient, when the detected temperature is lower than 37° C. (the normal body temperature), the temperature detecting means recognizes the end portion of the endoscope insertion portion as being outside of the body of the patient and outputs a detection signal. Further, it is desirable that the temperature detecting means be disposed at a safe position at a distance several centimeters from the stimulating light emitting end portion of the endoscope insertion portion.

In addition, the detecting means of the eigth fluorescent endoscope apparatus according to the present invention is provided with a gas detecting means disposed in the end portion of the endoscope insertion portion for detecting that the gas surrounding the end portion of the endoscope insertion portion differs from the gas inside the body of the patient, and a stimulating light emission prevention controlling means for preventing, via the stimulating light emission preventing means, the emission of stimulating light, based on the detection signal detected by the gas detecting means.

Here, the gas detecting means is a means for detecting the gases occurring within the body of a patient, which are of a higher temperature than those occurring outside the body of the patient. For example, there is a means for detecting carbon dioxide. However, and in short, any means may be used as far as it is capable of detecting the density of the gaseous component inside the body of a patient, which is of a higher density than that occurring outside of the body of the patient; for example, there are means for detecting methane, hydrogen sulfide, etc. Also, when taking a measurement, for cases in which a gas different from the outside air is injected into the body of a patient, the injected gas can also be detected. When the density of the detected gas is below a predetermined threshold value, the gas detecting means recognizes the end portion of the endoscope insertion portion as being outside of the body of the patient and outputs a detection signal. Further, it is desirable that the gas detecting means be disposed at a safe position at a distance several centimeters from the stimulating light emitting end portion of the endoscope insertion portion.

In addition, the detecting means of the tenth fluorescent endoscope apparatus according to the present invention is provided with a magnetic field producing means, which is mounted at the opening of the body orifice into which the endoscope insertion portion of the endoscope apparatus is to be inserted, for producing a magnetic field, and a magnetic field detecting means disposed in the endoscope insertion portion for detecting aforementioned magnetic field, and a stimulating light emission prevention controlling means for preventing, via the stimulating light emission preventing means, the emission of stimulating light, based on the detection signal detected by the magnetic field detecting means.

In addition, the detecting means of the eleventh fluorescent endoscope apparatus according to the present invention is provided with a light projecting means, which is mounted at the opening of the body orifice into which the endoscope insertion portion of the endoscope apparatus is to be inserted, for projecting light, and a reflected light detecting means for detecting the reflected light reflected by the endoscope insertion portion upon irradiation thereof by the projected light, and a stimulating light emission prevention controlling means for preventing, via the stimulating light emission preventing means, the emission of stimulating light, based on the detection signal detected by the reflected light detecting means.

In addition, the detecting means of the twelfth fluorescent endoscope apparatus according to the present invention is provided with a light projecting means mounted at the opening of the body orifice into which the endoscope insertion portion of the endoscope apparatus is to be inserted for projecting light, and a transmitted-light detecting means disposed in the endoscope insertion portion means for detecting the transmitted light transmitted by the endoscope insertion portion upon irradiation thereof by the projected light, and a stimulating light emission prevention controlling means for preventing, via the stimulating light emission preventing means, the emission of stimulating light, based on the detection signal detected by the transmitted-light detecting means.

In addition, the detecting means of the thirteenth fluorescent endoscope apparatus according to the present invention is provided with an airspace volume detecting means for detecting the airspace volume between the body of the patient and the endoscope insertion portion of the endoscope apparatus, and a stimulating light emission prevention controlling means for preventing, via the stimulating light emission preventing means, the emission of stimulating light, based on the detection signal detected by the airspace volume detecting means.

Here, the airspace volume is made to be of a predetermined uniform value when the endoscope insertion portion is in the body of a patient, and when the detected airspace volume is above the predetermined value, the airspace volume detecting means recognizes the end portion of the endoscope insertion portion as being outside of the body of the patient and outputs a detection signal.

In addition, the stimulating light emission prevention controlling means of the fourteenth fluorescent endoscope apparatus according to the present,invention is a stimulating light cut off means inserted into the optical path through which the stimulating light is guided to the section of which a measurement is to be taken.

In addition, the stimulating light emission prevention controlling means of the fifteenth fluorescent endoscope apparatus according to the present invention is a stimulating light standby means for controlling emission of the stimulating light by maintaining it in a standby state.

Here, the standby state refers to the ready-state of emitting stimulating light, for example, a state in which the voltage of the power source of the stimulating light source is reduced to a level below that required for operation of the stimulating light source, etc.; in short, any state in which the stimulating light standby means controls the stimulating light projecting means so that stimulating light is not emitted therefrom.

In addition, according to the sixteenth embodiment of the fluorescent endoscope apparatus according to the present invention, GaN type laser light is used as the stimulating light.

In addition, the seventeenth embodiment of the fluorescent endoscope apparatus according to the present invention comprises a projecting means for emitting stimulating light and illuminating light, a stimulating light guiding means for guiding stimulating light from the projecting means to the section of which a measurement is to be taken, an illuminating light emitting means for emitting illuminating light, an illuminating light guiding means for guiding illuminating light from the projecting means to the section of which a measurement is to be taken, an image detecting means for the image detecting a fluorescent image of the fluorescent light emitted from the section of which a measurement is to be taken upon irradiation thereof by stimulating light guided through the guiding means and a normal image of the light reflected from the section of which a measurement is to be taken upon irradiation thereof by the illuminating light, and a stimulating light controlling means for controlling the emission of stimulating light from the stimulating light projecting means, further comprising a power-source state detecting means for detecting that the power source of the fluorescent endoscope apparatus has been switched from the OFF to the ON state, a stimulating light emission preventing means for putting the stimulated light in an emission-prohibited state in which emission of stimulating light is prevented, an unlocking operation detecting means for detecting that a predetermined operation for unlocking the emission-prohibited state has been performed, and a stimulating light emission prevention controlling means for controlling the stimulating light emission preventing means so that the stimulating light is put in the emission-prohibited state when switching of the power-source from the OFF to the ON state is detected by the power-source state detecting means and so that the emission-prohibited state of the stimulating light is unlocked when aforementioned predetermined operation for unlocking the emission-prohibited state has been detected by the unlocking operation detecting means as having been performed.

According to the seventeenth fluorescent endoscope apparatus of the present invention, the power-source state detecting means detects that the state of the power source of the fluorescent endoscope apparatus has been switched from OFF to the ON, and detection data indicative thereof is transmitted to the stimulating light emission prevention controlling means. The stimulating light emission prevention controlling means causes operation of the stimulating emission preventing means and the stimulating light is put in the emission-prohibited state. Then, when the predetermined operation for unlocking the emission-prohibited state has been performed, this predetermined operation is detected by the unlocked-state operation detecting means, and detection data indicative thereof is transmitted to the stimulating light emission prevention controlling means. The stimulating light emission prevention controlling means causes operation of the stimulating emission preventing means and the stimulating light emission-prohibited state is unlocked.

Here, the expression "the power source of the fluorescent endoscope apparatus" means at least the power for turning the stimulating light projecting means ON. Further, in the state in which the power source is in the transitional state of having been switched from OFF to ON, the stimulating light projecting means does not operate until a predetermined threshold voltage has been attained. In addition the power-source state detecting means, the stimulating light emission prevention controlling means, and the stimulating light emission preventing means are activated at a faster timing than the stimulating light projecting means.

In addition, the eighteenth fluorescent endoscope apparatus according to the present invention can also be provided with a reset detecting means for detecting that the fluorescent endoscope apparatus has been reset. Here, "that the fluorescent endoscope apparatus has been reset" refers at least to the resetting of the stimulating light controlling means. When the fluorescent endoscope apparatus is detected by the reset detecting means as having been reset, detection data indicative thereof is transmitted to the stimulating light emission prevention controlling means. The stimulating light emission prevention controlling means causes operation of the stimulating emission preventing means and the stimulating light is put in the emission-prohibited state.

In addition, according to the nineteenth fluorescent endoscope apparatus according to the present invention, the stimulating light guiding means and the illuminating light guiding means are disposed within the endoscope insertion portion. The nineteenth fluorescent endoscope apparatus according to the present invention is provided with a connection detecting means for detecting whether or not the stimulating light guiding means and the stimulating light projecting means are connected, whether or not the illuminating light projecting means and the illuminating light guiding means are connected and whether or not the endoscope insertion portion and the image signal processing portion are connected, and by detection that of even one of the following: that the stimulating light projecting means and the stimulating guiding means are not connected; that the illuminating light projecting means and the illuminating light guiding means are not connected; or that the endoscope insertion portion and the image processing portion are not connected, the stimulating light emission prevention controlling means causes operation of the stimulating light emission preventing means and the stimulating light can be put in the emission-prohibited state.

The "endoscope insertion portion" refers to the portion of the fluorescent endoscope apparatus that is inserted into and can be removed from the patient's body and which can be exchanged and cleaned. The image processing portion includes at least the portion for performing image processing on an image detected fluorescent image.

In addition, the stimulating light emission prevention controlling means of the twentieth fluorescent endoscope apparatus according to the present invention is a stimulating light cutoff means inserted into the:.optical path through which the stimulating light is guided to the section of which a measurement is to be taken.

In addition, the stimulating light emission prevention controlling means of the twenty-first fluorescent endoscope apparatus according to the present invention is a stimulating light standby means for controlling emission of the stimulating light by maintaining it in a standby state.

In addition, the twenty-second fluorescent endoscope apparatus according to the present invention is also provided with a stimulating light emission prevention data recording means for recording control data for controlling aforementioned stimulating light emission preventing means; when the power-source state detecting means detects that the power source has been switched from OFF to ON, or when the reset detecting means detects that the stimulating light emission prevention controlling means has been reset, the stimulating light emission prevention controlling means reads the control data recorded in the stimulating light emission prevention control data recording means, and controls the stimulating light emission preventing means so that the stimulating light can be put in the emission-prohibited state. Note that for cases in which the stimulating light emission preventing means is a stimulating light cutoff means, the control data recorded in the stimulating light emission prevention control data recording means is control data for controlling the stimulating light cutoff means, and for cases in which the stimulating light emission preventing means is a stimulating light standby means, the control data recorded in the stimulating light emission prevention control data recording means is control data for controlling the stimulating light standby means.

For cases in which the stimulating light emission preventing means is a stimulating light cutoff means, when the power source is switched from OFF to ON and the power-source state detecting means detects that the power source has been switched from OFF to ON, or when the fluorescent endoscope apparatus is reset and the reset detecting means detects that this state has been reset, the stimulating light emission prevention controlling means reads the control data recorded in the stimulating light emission prevention control data recording means, and causes operation of the stimulating light cutoff means so that the stimulating light can be put in the emission-prohibited state.

In addition, for cases in which the stimulating light emission preventing means is a stimulating light standby means, when the power source is switched from OFF to ON and the power-source state detecting means detects that the power source has been switched from OFF to ON, or when the fluorescent endoscope apparatus is reset and the reset detecting means detects that this state has been reset, the stimulating light emission prevention controlling means reads the control data recorded in the stimulating light emission prevention control data recording means, and causes operation of the stimulating light standby means so that the stimulating light can be put in the emission-prohibited state.

Further, the predetermined operation for unlocking the emission-prohibited state of the stimulating light may be an operation of any type as far as it is a mandatory operation to be performed before an actual operation to take a measurement or to perform maintenance.

In addition, according to the twenty-third fluorescent endoscope apparatus of the present invention, aforementioned predetermined operation for unlocking the emission-prohibited state of the stimulating light is a manually performed operation. For example, throwing a switch, a touch-panel input operation, and etc.; further, a combination of these operations can be performed. In this case, the emission-prohibited state of the stimulating light is unlocked only when a combination of operations has been performed. Further, operations performed only when maintenance operations are to be commenced and operations to be performed only when the measurement procedure is to be commenced can also be combined.

In addition, according to the twenty-fourth fluorescent endoscope apparatus of the present invention, aforementioned manually performed operation is an operation of inputting the patient data. Note that the operation of inputting the patient data is such that it's performance is required in order to perform operations for taking an actual measurement, and such that pseudo patient information must be input in order to perform maintenance operations. Any appropriate data for initiating maintenance operations can be used as pseudo patient data.

In addition, according to the twenty-fifth embodiment of the fluorescent endoscope apparatus of the present invention, GaN type laser light is used as the stimulating light.

According to the first fluorescent endoscope apparatus of the above described configuration according to the present invention, which is provided with a detecting means for detecting that the end portion of the endoscope insertion portion is outside of the body of the patient, because the stimulating light emission preventing means prevents the emission of stimulating light, based on the detection signal of the detecting means, the stimulating light does not enter the eyes of the patient and cause injury thereto, and safety is ensured.

In addition, according to the second fluorescent endoscope apparatus of the present invention, in which the detecting means is provided with a flicker detecting means for detecting the flicker appearing due to the light illuminating the inside of the diagnosis room, when the flicker detecting means detects the presence of flicker, the end portion of the endoscope insertion portion is recognized as being located outside the body of the patient and a detection signal is output to the stimulating. light emission prevention controlling means, and at that time, because the stimulating light emission prevention controlling means prevents the emission of stimulating light, the stimulating light does not enter the eyes of the patient and cause injury thereto, and safety is ensured. Further, the degree of safety can be further increased if the flicker detecting means be disposed at a safe position at a distance several centimeters from the stimulating light emitting end portion of the endoscope insertion portion.

In addition, according to the third fluorescent endoscope apparatus of the present invention, in which the detecting mean is provided with a brightness distribution detecting means for detecting the brightness distribution of a normal image. When the brightness distribution detecting means detects a brightness distribution differing from that occurring when the endoscope insertion portion is inside the body of a patient, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured.

In addition, according to, the fourth fluorescent endoscope apparatus of the present invention, in which the detecting means is provided with a brightness detecting means for detecting the brightness of a normal image. When the brightness detecting means detects that the brightness of any of the pixels of a normal image is larger than a predetermined threshold value, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured.

In addition, according to the fifth fluorescent endoscope apparatus of the present invention, in which the detecting means is provided with a color signal detecting means for detecting the color signal of a normal image. When the color signal detecting means detects that the R signal of the RGB signal of each pixel of a normal image is smaller than a predetermined threshold value, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured.

In addition, according to the sixth fluorescent endoscope apparatus of the present invention, in which the detecting means is provided with a straight-line detecting means for detecting the straight-line pattern of a normal image . When the straight-line detecting means detects a straight-line component larger than a predetermined threshold value, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured.

In addition, according to the seventh fluorescent endoscope apparatus of the present invention, in which the detecting means is provided with a light strength detecting means for detecting the light strength occurring near the side of the end portion of the endoscope insertion portion. When the light strength detecting means detects a light strength occurring near the side of the end portion of the endoscope insertion portion that is larger than a predetermined threshold value, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured. Further, the degree of safety can be further increased if the flicker detecting means be disposed at a safe position at a distance several centimeters from the very stimulating light emitting end of the endoscope insertion portion.

In addition, according to the eighth fluorescent endoscope apparatus of the present invention, in which the detecting means is provided with a temperature detecting means for detecting the temperature occurring near the side of the end portion of the endoscope insertion portion. When the temperature detecting means detects a temperature occurring near the side of the end portion of the endoscope insertion portion that is lower than 37° C. (the normal body temperature of a patient), the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured. Further, the degree of safety can be further increased if the flicker detecting means be disposed at a safe position at a distance several centimeters from the very stimulating light emitting end of the endoscope insertion portion.

In addition, according to the ninth fluorescent endoscope apparatus of the present invention, in which the detecting means is provided with a gas detecting means for detecting the gas occurring near the side of the end portion of the endoscope insertion portion. When the gas detecting means detects that the density of, for example, the density of the carbonic acid gas occurring near the side of the end portion of the endoscope insertion portion is lower than a predetermined threshold value, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured. Further, the degree of safety can be further increased if the flicker detecting means be disposed at a safe position at a distance several centimeters from the very stimulating light emitting end of the endoscope insertion portion.

In addition, according to the tenth fluorescent endoscope apparatus of the present invention, in which the detecting means is provided with a magnetic field producing means mounted at the opening of the body orifice of the patient into which the insertion portion of the endoscope apparatus is to be inserted for producing a magnetic field, and a magnetic field detecting means for detecting aforementioned magnetic field. Based on detection by the magnetic field detecting means of a magnetic field produced by the magnetic field producing means, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured.

In addition, according to the eleventh fluorescent endoscope apparatus of the present invention, in which the detecting means is provided with a light projecting means mounted at the opening of the body orifice into which the insertion portion of the endoscope apparatus is to be inserted for projecting light, and a reflected light detecting means for detecting the reflected light reflected by the endoscope insertion portion upon irradiation thereof by the projected light. Based upon detection by the reflected light detecting means of reflected light, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured.

In addition, according to the twelfth fluorescent endoscope apparatus of the present invention, in which the detecting means is provided with a light projecting means mounted at the opening of the body orifice into which the insertion portion of the endoscope apparatus is to be inserted for projecting light, and a transmitted-light detecting means for detecting the transmitted light transmitted by the endoscope insertion portion upon irradiation thereof by the projected light. Based upon detection by the transmitted light detecting means of transmitted light, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured.

In addition, according to the thirteenth fluorescent endoscope apparatus of the present invention, in which the detecting means is provided with an airspace volume detecting means for detecting the airspace volume between the body of the patient and the endoscope insertion portion. When the airspace volume detecting means detects an airspace volume of a size larger than a predetermined threshold value, the end portion of the endoscope insertion portion is recognized as being located outside the body of the patient and a detection signal is output to the stimulating light emission prevention controlling means, and at that time, because the stimulating light emission prevention controlling means prevents the emission of stimulating light, the stimulating light does not enter the eyes of the patient and cause injury thereto, and safety is ensured.

In addition, according to the fourteenth fluorescent endoscope apparatus of the present invention, because the stimulating light emission preventing means is a cutoff means disposed within the optical path through which the stimulating light is guided to the section of which a measurement is to be taken, there is no necessity to provide a new device, and prevention of the emission of stimulating light can be controlled solely by the control signal.

In addition, according to the fifteenth fluorescent endoscope apparatus according of the present invention, because the stimulating light emission prevention controlling means the is a stimulating light standby means for controlling emission of the stimulating light by maintaining it in a standby state, there is no necessity to provide a new device, and prevention of the emission of stimulating light can be controlled solely by the control signal.

In addition, according to the sixteenth embodiment of the fluorescent endoscope apparatus according to the present invention, because GaN type laser light is used as the stimulating light, fluorescent light is efficiently emitted from the section of which a measurement is being taken, and the apparatus can be of a small size.

In addition, according to the seventeenth fluorescent endoscope apparatus of the present invention, because the stimulating light is in definitely in the emission-prohibited state when the system is started, when a measurement is initiated, or when maintenance operations are to be commenced, the safety of the operator, the patient and personnel performing maintenance, with respect to the inadvertent emission of stimulating light, is ensured.

In addition, according to the eighteenth fluorescent endoscope apparatus of the present invention, because the stimulating light is definitely in the emission-prohibited state when the system is reset, the safety of the operator, the patient and personnel performing maintenance, with respect to the inadvertent emission of stimulating light, is ensured.

When the system is started, the power-source state detecting means detect that the power source has been switched from the OFF to the ON position, detection data indicative thereof is transmitted to the stimulating light emission prevention controlling means. At this time, the stimulating light emission prevention controlling means reads in the control data recorded in the stimulating light emission prevention control data recording means for controlling the stimulating light emission preventing means, and causes the operation of the stimulating light emission preventing means; the stimulating light is put in the emission-prohibited state.

When the fluorescent endoscope apparatus is detected by the reset detecting means as having been reset, detection data indicative thereof is transmitted to the stimulating light emission prevention controlling means, after which, the stimulating light is put in the emission-prohibited state in the same way as when the system is started.

When the predetermined operation for unlocking the emission-prohibited state of the stimulating light is performed, this operation is detected by the unlocking operation detecting means, and detection data indicative thereof is transmitted to the stimulating light emission prevention controlling means. At this time, the stimulating light emission prevention controlling means causes the operation of the stimulating light emission prevention means and the emission-prohibited state of the stimulating light is unlocked. By making this predetermined operation a required operation to be performed in order to take a measurement, the stimulating light is definitely in the emission-prohibited state when operations to take a measurement are initiated.

Further, when changing patients, the endoscope insertion portion must be removed from the signal processing portion to be cleaned and exchanged. That the end portion of the endoscope insertion portion has been removed from the signal processing portion is detected by the connection detecting means, and detection data indicative thereof is transmitted to the stimulating light emission prevention controlling means; in the same way as described above, the stimulating light is put in the emission-prohibited state. Because this emission-prohibited state is unlocked by performance of a predetermined operation in the same way as described above, even for cases in which patients are changed, the stimulating light is definitely in the emission-prohibited state.

Still further, when maintenance is to be performed, by requiring that aforementioned predetermined operation be performed before maintenance can be performed, when maintenance operations are initiated, the stimulating light is definitely in the emission-prohibited state.

In addition, according to the nineteenth fluorescent endoscope apparatus of the present invention, for cases in which the endoscope insertion portion is removed from the signal processing portion for maintenance, that the endoscope insertion portion has been removed is detected by the connection detecting means; the stimulating light is put in the emission-prohibited state and the safety of the personnel performing maintenance is ensured. However, it is not mandatory that the insertion portion be used when maintenance is performed; there are cases which emission of stimulating light is required with the insertion portion having been removed from the signal processing portion. Therefore, for example, by inserting a dummy insertion portion into the image processing portion, the stimulating light can be made to not go into the emission-prohibited state. "Pseudo plugging in of the insertion portion" refers to, for example, plugging into the image signal processing portion instead of the real endoscope insertion portion, in short, any method by which the insertion portion is not detected as being removed will suffice.

In addition, according to the twentieth fluorescent endoscope apparatus of the present invention, because the stimulating light emission prevention controlling means is a stimulating light cutoff means inserted into the optical path through which the stimulating light is guided to the section of which a measurement is to be taken, the emission of stimulating light can be controlled by an apparatus of a simple configuration.

In addition, according to the twenty-first fluorescent endoscope apparatus of the present invention, because the stimulating light emission prevention controlling means is a stimulating light standby means for controlling emission of the stimulating light by maintaining it in a standby state, there is no necessity to provide a new device, and the prevention of the emission of stimulating light can be controlled be only the control signal.

In addition, according to the twenty-second fluorescent endoscope apparatus of the present invention, because the stimulating light emission preventing means is also provided with a stimulating light emission prevention data recording means for recording control data for controlling aforementioned stimulating light emission preventing means, and when the power-source state detecting means detects that the power source has been switched from OFF to ON, or when the reset detecting means detects that the stimulating light emission prevention controlling means has been reset, the stimulating light emission prevention controlling means reads the control data recorded in the stimulating light emission prevention control data recording means and controls the stimulating light emission preventing means so that the stimulating light can be put in the emission-prohibited state, control of the stimulating light emission preventing means can be performed more simply and easily.

In addition, according to the twenty-third fluorescent endoscope apparatus of to the present invention, because aforementioned predetermined operation for unlocking the emission-prohibited state of the stimulating light is a manually performed operation, it can be confirmed that the apparatus is in a safe operational state before performing the operation to unlock the emission-prohibited state of the stimulating light.

In addition, according to the twenty-fourth fluorescent endoscope apparatus of the present invention, because because aforementioned manually performed operation is an operation of inputting the patient data, it is not necessary to provide a new device solely for the purpose of unlocking the emission-prohibited state of the stimulating light.

In addition, according to the twenty-fifth embodiment of the fluorescent endoscope apparatus of the present invention, because GaN type laser light is used as the stimulating light, fluorescent light is emitted efficiently from the section of which a measurement is to be taken, and the apparatus can be of a small size.

BRIEF DESCRIPTION OF THE DRAWINGS

FIG. 12 is a schematic drawing of a fluorescent endoscope apparatus according to the twelfth embodiment of the present invention, FIG. 16 is a timing chart of the exposure and readout of normal images and fluorescent images occurring in the fluorescent endoscope apparatuses according to the thirteenth and fourteenth embodiments of the present invention.

DESCRIPTION OF THE PREFERRED EMBODIMENTS

Figure 1:
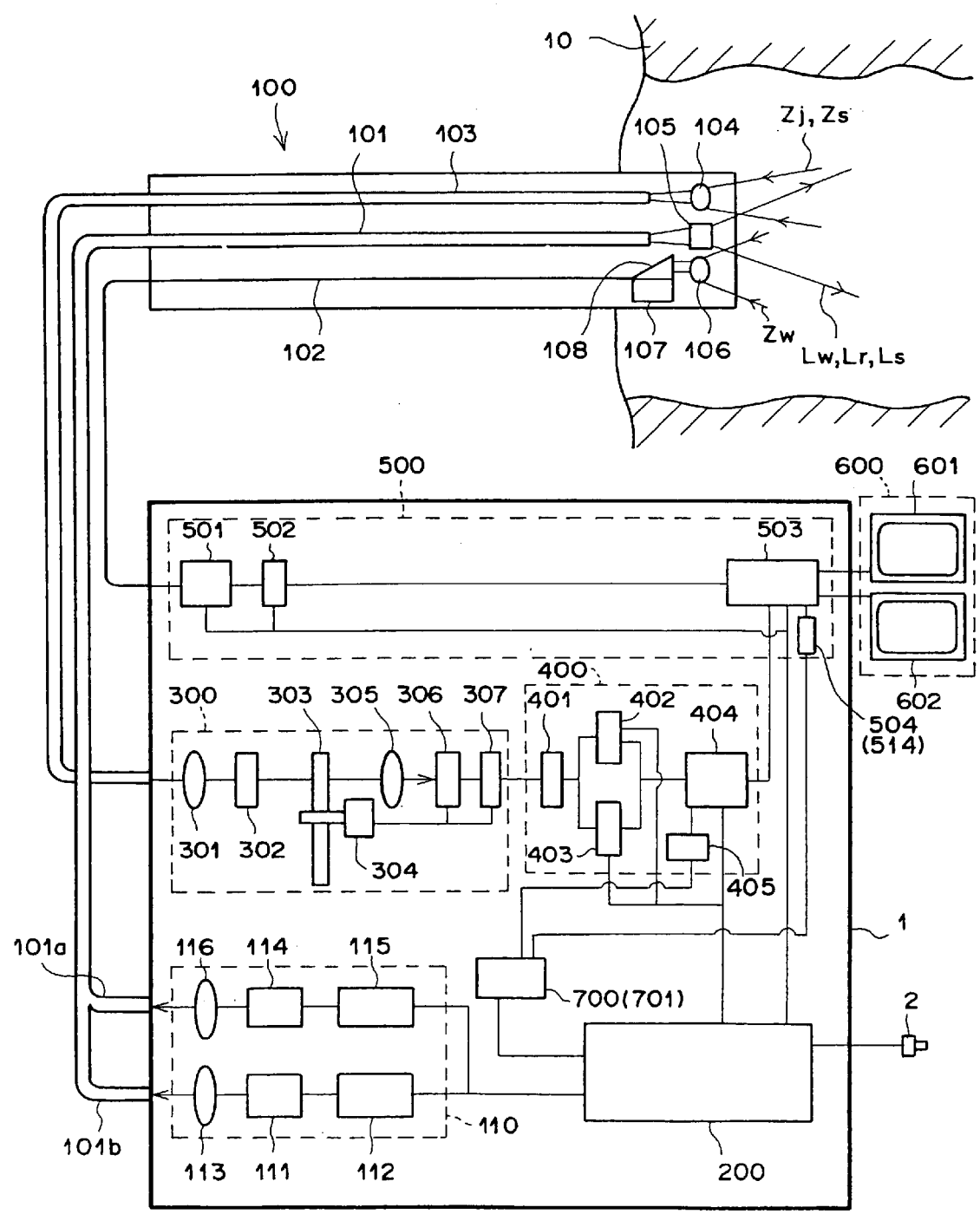
FIG. 1 is a schematic drawing of a fluorescent endoscope apparatus according to the first and second embodiments of the present invention.

Hereinafter, the preferred embodiments of the present invention will be explained with reference to the drawings. FIG. 1 is a schematic drawing of the fluorescent endoscope apparatus according to the present invention.

The fluorescent endoscope apparatus according to the present invention comprises an endoscope insertion portion 100 for insertion into suspected infection areas of a patient, an image signal processing portion 1 for processing as an image signal the data obtained of the tissue in the section of which a measurement has been taken, a monitor 600 for displaying as a visible image the signal processed by the image signal processing portion, and a switch 2 for switching from the normal image detecting state to the fluorescent image detecting state. The image processing portion 100 comprises an illuminating unit 110 which is provided with two light sources for emitting normal-image use white light Lw and reflected-image use reference light Ls, and autofluorescent-light image use stimulating light Lr, respectively; an image detecting unit 300 for the image detecting the autofluorescent-light image Zj formed of fluorescent light having a two different wavelength ranges, which has been emitted from the living-tissue subject upon irradiation thereof by stimulating light, and the reflected image reflected from the living-tissue subject upon irradiation thereof by reference light, and converting said images to digital values and outputting two-dimensional image data; an image computing unit 400 for calculating the distance correction, etc. of the two-dimensional image data of the autofluorescent-light image output from image processing unit 300 and computing a computed image, for allocating the color data, for allocating brightness data to the two-dimensional image data of the reflected image, and for combining and outputting the 2 image data, a display signal processing unit 500 for digitizing the normal image as a two-dimensional image data, and converting said two-dimensional image data an d the signal output from the image computing unit 400 to a video signal and outputting said video signal, a control-use computer 200 connected to each unit for controlling the operation timing thereof, stimulating light emission prevention controlling means 700 for preventing the emission of stimulating light when flicker is detected by the flicker detecting means 504 of the display signal processing unit 500 or the flicker detecting means 405 of the image computing unit 400.

The endoscope insertion portion 100 comprises a light guiding portion 101 extending to the forward end portion of the inside portion thereof, a CCD cable 102 and an image fiber 103. The forward end portion of light guiding portion 101 and CCD cable 102, that is, the forward end portion of endoscope insertion portion 100 is provided with an illumination lens 104 and an objective lens 105. Further, the image fiber 103 is formed of silica optical fiber, and is provided with a focusing lens 106 at the forward end thereof. There is a normal-image detecting element 107 connected to the forward end portion of the CCD cable 102, and a reflection-use prism 108 is attached to said normal-image detecting element 107. The light guide 101 is formed of a composite glass fiber white light guide 101a bundled together with a silica optical fiber stimulating light guide 101b, and is in the form of an integrated cable; the white light guide 101a and the stimulating light guide 101b are connected to the illuminating unit 110. On end portion of the CCD cable 102 is connected to the display signal processing unit 500, and one end portion of the image fiber 103 is connected to the image detecting unit 300.

The illuminating unit 110 comprises a white light source 114 for emitting normal-image use white light Lw, a white-light source use power source 115 electrically connected to said white light source 114, a white-light use focusing lens 116 for focusing the white light Lw emitted from the white light source 114, a GaN type semiconductor laser 111 for emitting fluorescent-image use stimulating light Lr, a semiconductor-laser use power source 112 electrically connected to said GaN type semiconductor laser 111, and a stimulating-light use focusing lens 113 for focusing the stimulating light emitted from the GaN type semiconductor laser 111. Further, because the white light Lw emitted from the white light source 114 includes wavelength ranges that can be used as the reference light Ls, it can also be used as the reference light source.

The image detecting unit 300 is connected to the image fiber 103, and comprises a fluorescent-light use collimator lens 301 for guiding the autofluorescent-light image and the reflected-light image conveyed via the image fiber 103 to a focusing optical system, a stimulating light cutoff filter 302 for cutting off from the autofluorescent-light image the wavelengths of light close to that of the stimulating light, an optical transmitting filter 303 for extracting the desired wavelengths of light from the autofluorescent-light image and the reflected-light image passing through the cutoff filter 302, a filter rotating apparatus 304 for rotating said optical transmitting filter 303, a fluorescent-light use focusing lens 305 for focusing the autofluorescent-light image and the reflected-light image passing through the cutoff filter 302, a fluorescent-image use high sensitivity image detecting element 306 for detecting the autofluorescent-light image and the reflected-light image focused by said fluorescent-light use focusing lens 305, and an AD converter 307 for digitizing the autofluorescent-light image and the reflected image detected by said fluorescent-image use high sensitivity image detecting element 306 and outputting the digitized value as a two-dimensional image data.

Figure 2:
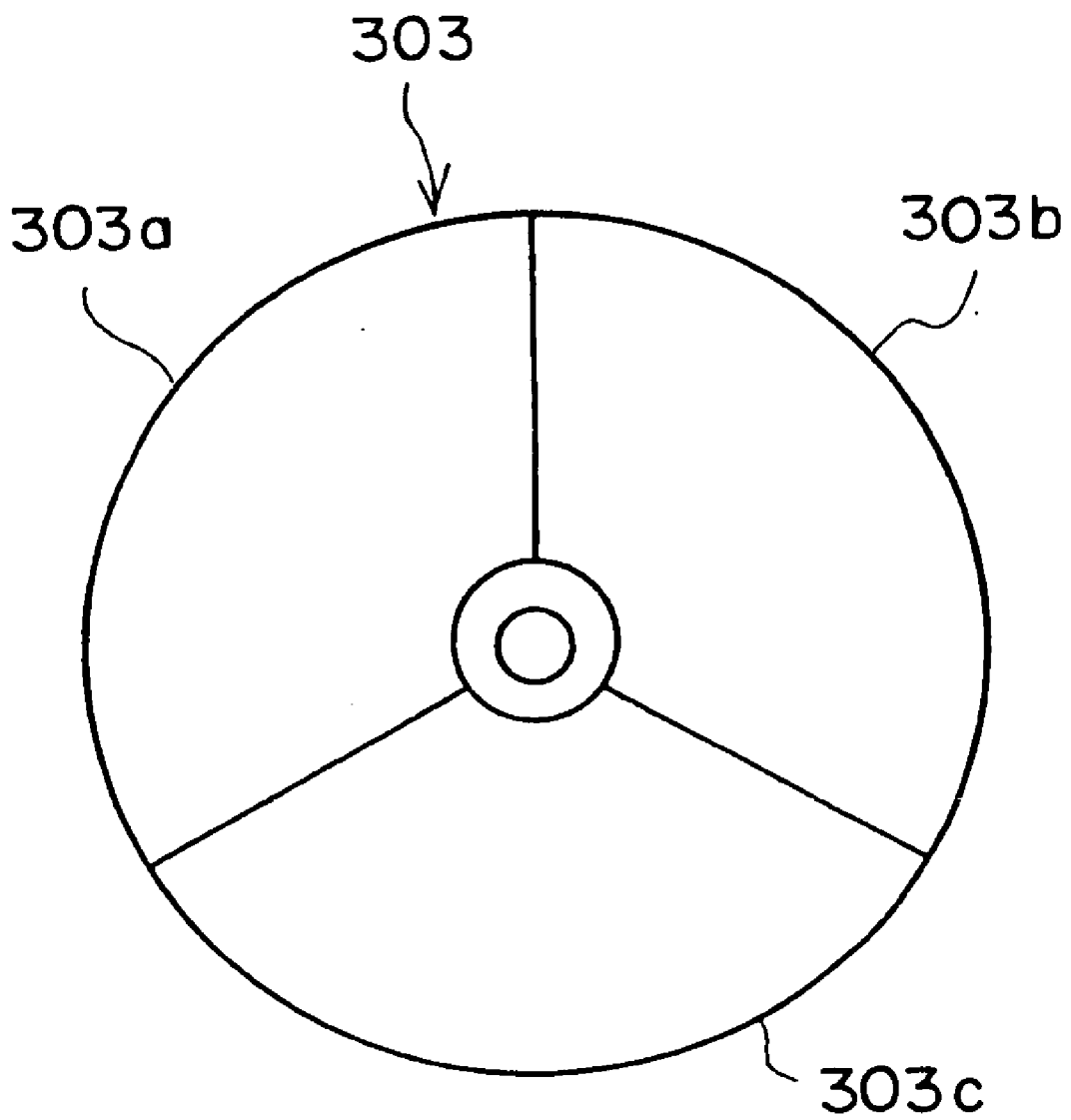
FIG. 2 is a schematic drawing of an embodiment of an optical transmitting filter employed in embodiments 1–12 of the fluorescent endoscope apparatus according to the present invention.

As shown in FIG. 2, the optical transmitting filter 303 comprises three types of band-pass filters 303a, 303b and 303c: band-pass filter 303a transmits light in the wavelength range of 430 nm to 730 nm; band-pass filter 303b transmits light in the wavelength range of 430 nm to 530 nm; and band-pass filter 303c transmits light in the wavelength range of 750 nm to 900 nm.

The image computing unit 400 comprises an image-use memory 401 for remembering the digitized autofluorescent-light image of two different wavelength bands and the reflected-light image, an autofluorescent-light image computing portion 402 for computing, according to the ratio of each pixel value of each of the autofluorescent-light image formed of two different wavelength bands of fluorescent light that has been remembered in the memory 401, the computed value of each pixel and assigning a color value to said computed value, a reflected-light image computing means for assigning a brightness value to each pixel value of the reflected-light image remembered in the memory 401, an image composing means 404 for combining the image signal having color data output from the fluorescent image computing portion 402 and the image signal having color data output from the reflected-light image computing portion 403, and a flicker detecting means 405 for detecting flicker from the image. composed by the image composing means 404.

The image-use memory 401 comprises a narrow band fluorescent image memory zone, which is not shown in the drawings, a wide band fluorescent image memory zone, and a reflected-light image memory zone. The fluorescent image transmitted through the band-pass filter 303a is stored in the wide band fluorescent image memory zone, the fluorescent image transmitted by the band-pass filter 303b is stored in the narrow band fluorescent image memory zone, and the fluorescent image transmitted by the band-pass filter 303c is stored in the reflected-light image memory zone.

The image signal processing unit 500 comprises an AD converter 501 for digitizing the visible image signal obtained by the normal image detecting element 107, a normal-image use memory 502 for storing the digitized normal image signal, a video signal processing circuit 503 for converting the image signal output from the normal-image use memory 502 and the composite image signal output from the image composing portion 404, and a flicker detecting means 504 for detecting flicker from the image signal of the normal image.

The monitor unit 600 comprises a normal-image use monitor 601 and a composite image use monitor 602.

Next, the operation of a fluorescent endoscope implementing the configuration described above according to the current embodiment of the fluorescent endoscope apparatus of the present invention will be explained.

First, the operation for cases in which an autofluorescent-light image formed of two different wavelength bands of fluorescent light and a reflected-light image are used to form a composite image and said composite image is displayed will be explained.

When an autofluorescent-light image formed of two different wavelength bands of fluorescent light is detected, the semiconductor-use power source. is activated, based on a signal from the control computer 200, and the GaN type semiconductor laser 111 emits the stimulating light Lr, which has a wavelength of 410 nm. The stimulating light Lr passes through the stimulating-light use focusing lens 113 and enters the stimulating light cutoff filter 101b, and after being guided to the forward end portion of the endoscope insertion portion 150, is projected from the illuminating lens 103 onto the living-tissue subject 10.

The autofluorescent-light image emitted from the living-tissue subject 10 upon irradiation thereof by the stimulating light Lr is focused by the focusing lens 105 and guided to the forward end portion of the image fiber 103; it then passes through the image fiber 103 and enters the stimulating light cutoff filter 302. The autofluorescent-light image that passes through the stimulating light cutoff filter 302 enters the optical transmitting filter 303. Note that the stimulating light cutoff filter 302 is a band-pass filter that transmits all fluorescent light having a wavelength of 420 nm or larger. Because the stimulating light Lr has a wavelength of 410 nm, the stimulating light reflected from the living-tissue subject 10 is cutoff by the stimulating light cutoff filter 302 and does not enter the optical transmitting filter 303.

The filter rotating apparatus 304 is activated by the control computer 200, and after the autofluorescent-light image zj passes through the band-pass filter 303a, it is focused by the fluorescent-light use focusing lens 305 and detected by the fluorescent-image use high-sensitivity detecting element 306 as a wide-band autofluorescent-light image, and after passing through the band-pass filter 303b, it is detected as a narrow-band autofluorescent-light image by the fluorescent-image use high-sensitivity detecting element 306, and after the autofluorescent-light image Zj is input to the AD converting circuit 307 from the fluorescent-image use high-sensitivity detecting element 306 and digitized therein, it is stored in the image data memory 401. Note that the wide-band autofluorescent-light image detected by the fluorescent-image use high-sensitivity detecting element 306 is stored in the wide-band autofluorescent-light image memory zone, and the narrow-band autofluorescent-light image is stored in the narrow-band autofluorescent-light image memory zone.

When a reflected-light image is detected, the power source of the white light source is activated, based on a signal from the control computer 200, and the white light Lw is emitted. This white light Lw contains the reference light Ls, which falls in the wavelength range of 750 nm to 900 nm. The white light Lw containing the reference light Ls passes through the white-light use focusing lens 116 and enters the white light guide 101a, and after being guided to the forward end portion of the endoscope insertion portion, it is projected from the illuminating lens 103 onto the living-tissue subject 10.

The reflected-light image formed of the reflected white light Lw containing the reference light Ls reflected from the living-tissue subject 10 upon irradiation thereof by the white light Lw containing the reference light Ls is focused by the focusing lens 105 and enters the forward end portion of the image fiber 103; it then passes through the image fiber 103 and enters the stimulating light. cutoff filter 302. The reflected-light image passing through the stimulating light cutoff filter 302 enters the optical transmitting filter 303.

The filter rotating apparatus 304 is activated by the control computer 200, and after the reflected-light image passes through the band-pass filter 303c, it is focused by the fluorescent-light use focusing lens 305, detected by the and the visible image signal thereof is input to the AD converting circuit 307 from the fluorescent-image use high-sensitivity detecting element 306, and after being digitized by the AD converting circuit 307, it is stored in the image data memory 401. Here, the reflected image formed of the reflected light reflected from the living-tissue subject 10 upon illumination thereof by the white light Lw containing the reference light Ls passes through the band-pass filter 303c. In addition, the reflected-light image detected by the fluorescent-image use high-sensitivity detecting element 306 is stored in the reflected-light image storage zone of the image memory 401. The autofluorescent-light image computing portion 402 computes a computed value for each pixel, according to the ratio of each pixel, of each image, and assigns color data to each of said computed values, forms an image signal having color data, and outputs said image signal having color data. In addition, the reflected-light image computing portion 403 assigns brightness data to each pixel value of the reflected-light image stored in the image memory 401, forms an image signal having color data, and outputs said image signal having color data. The two image signals output from autofluorescent-light image computing portion 402 and the reflected-light image computing portion 403 are combined by the image composing portion 404. The composite image composed by the image composing portion 404 is input to the monitor unit 600 after being DA converted by the video signal processing circuit 503, and is displayed on the composite image use monitor 602.

Next, the operation for when a normal image is to be displayed will be explained. When a normal image is to be displayed, the white-light source power source is activated, based on a signal from the control computer 200, and the white light Lw is emitted from the white light source 114. The white light Lw passes through the white-light use focusing lens 116 and enters the white light guide 101a, and after being guided to the forward end portion of the endoscope insertion portion 100, the white light Lw is projected onto the living-tissue subject 10 from the illuminating lens 103. The white light Lw reflected from the living-tissue subject is focused by the objective lens 106 and reflected by the reflection-use prism 108, and is detected by the normal-image detecting element 107. The visible image signal from the normal-image detecting element 107 is input to the AD converter 501, and after being digitized therein, is stored in the normal-image memory 502. After the normal image stored by the normal-image memory 502 is processed into a color image signal (RGB signal) by the video signal processing circuit 503, it is input to the monitor unit 600 after being DA converted, and is displayed on the normal-image use monitor 601 as a visible image.

The continuous operation described above occurring when a composite image and a reflected-light image are displayed is controlled by the control computer 200. Further, the when the endoscope insertion portion 100, is inserted into the body of a patient, it is inserted in the normal-image detecting state, and by depressing a switch 2, it can be switched for detecting a normal-image, an autofluorescent-light image or a reflected-light image. Note that while a measurement is being taken, detecting of an autofluorescent-light image, a reflected-light image and a normal image can be performed alternately in a time division manner. When the endoscope insertion portion 100 is removed after a measurement has been taken, by depressing the switch 2, the endoscope insertion portion 100 can be switched to the. normal-image detecting state.

Here, during detecting a normal image, an autofluorescent-light image or a reflected-light image, when the forward end portion of the endoscope insertion portion. 100 is outside the body of the patient, the flicker occurring due to the light used for illuminating the diagnosis room, which would be detected together with the normal image, the autofluorescent-light image or the reflected-light image by the fluorescent-image use high-sensitivity detecting element 306 or the normal-image detecting element 107, is detected by the flicker detecting means 405 or the flicker detecting means 504. When flicker is detected by the flicker detecting means 405 or 504, a detection signal is output therefrom to the stimulating light emission prevention controlling means 700, and said stimulating light emission prevention controlling means 700, by use of the controlling computer 200, turns off the semiconductor laser.-use power source 112 the and prevents the emission of the stimulating light. Further, at this point, even if the switch 2 is depressed, the stimulating light is not be emitted. Note that the stimulating light emission preventing means of the present invention is combined with the control computer 200.

According to the fluorescent endoscope apparatus of the configuration described above, a flicker detecting means is provided for detecting the flicker occurring due to the light used for illuminating the diagnosis room, and when said flicker detecting means detects the presence of flicker, the forward end portion of the insertion portion is recognized as being located outside the body of the patient and the flicker detecting means outputs a detection-signal to the stimulating light emission prevention controlling means, and because the stimulating light emission prevention controlling means prevents the emission of stimulating light, the safety of the patient and the operator can be ensured.

Next, the fluorescent endoscope apparatus according second embodiment of the present invention will be explained. Because the configuration of the fluorescent endoscope apparatus according to the second embodiment is substantially the same as that of the first embodiment shown in FIG. 1, only elements differing from the first embodiment are given revised element reference numbers in FIG. 1. Note that in so far as further explanation of the same elements occurring in the first embodiment is not particularly required, it has been omitted.

Instead of the flicker detecting 405 or 504 of the first embodiment, the fluorescent endoscope apparatus according to the current embodiment is provided with a brightness distribution detecting means 514 for detecting the brightness distribution of a normal image.

Next, the operation of the fluorescent endoscope apparatus according to the current embodiment will be explained. According to the fluorescent endoscope apparatus of the current embodiment, the brightness distribution of the digital data of each pixel of a normal image detected by the normal-image detecting element 107 is detected by a brightness distribution detecting means 514. When the brightness distribution of the digital data of each pixel of a normal image shows that the brightness signal occurring at the center of an image is larger than the brightness signal occurring at the circumference of an image, the brightness distribution detecting means recognizes that the forward end portion of the endoscope insertion portion 100 is outside the body of the patient and outputs a detection signal to the stimulating light emission prevention controlling means 701. The stimulating light emission prevention controlling means 701 turns the semiconductor-use power source 112 off, by use of the control computer 112, and prevents the emission of stimulating light.

According to the fluorescent endoscope apparatus of the configuration described above, a brightness distribution detecting means is provided for detecting the brightness distribution of a normal image, and when said brightness distribution detecting means detects a brightness distribution state different from that occurring when the forward end portion of the endoscope insertion portion 100 is inside the body of a patient, the forward end portion of the insertion portion is recognized as being located outside the body of the patient and the brightness distribution detecting means outputs a detection signal to the stimulating light emission prevention controlling means, and because the stimulating light emission prevention controlling means prevents the emission of stimulating light, the safety of the patient and the operator can be ensured.

Figure 3:
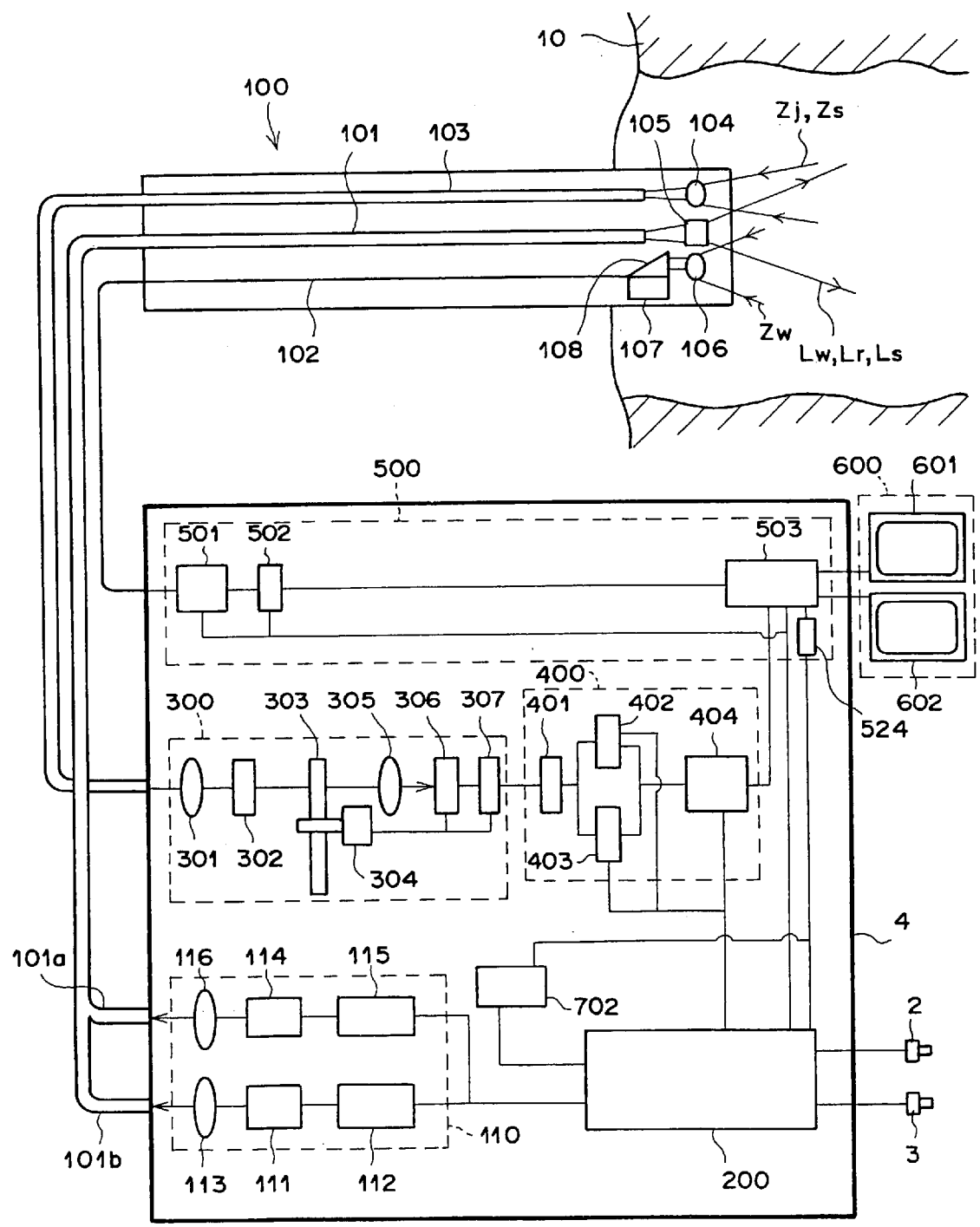
FIG. 3 is a schematic drawing of a fluorescent endoscope apparatus according to the third embodiment of the present invention.

Next, the fluorescent endoscope apparatus according third embodiment of the present invention will be explained. FIG. 3 is a schematic drawing of the configuration of a fluorescent endoscope apparatus according to the third embodiment of the present invention. Note that in so far as further explanation of the same elements occurring in the first embodiment is not particularly required, it has been omitted.

The fluorescent endoscope apparatus according to the third embodiment of the present invention comprises a brightness detecting means 524 for detecting the degree of brightness of each pixel of a normal image, and a white-light switch 3 for turning off the white-light use power source 115.

Next, the operation of the fluorescent endoscope apparatus according to the current embodiment will be explained. First, with the white-light use power source 115 in the off state, the endoscope insertion portion 100 is inserted into the body of the patient using the sight of the operator. After insertion, a normal image is detected and the brightness of each pixel of the normal image is detected by the brightness detecting means 524. If the brightness of any of the pixels of the normal image is above a predetermined threshold value, the brightness detecting means 524 sends a detection signal to the control computer 200, and the control computer 200 turns the white-light use power source on. Subsequently, by depressing the switch 2, the stimulating light is caused to be emitted and the autofluorescent-light image detecting state is thereby brought about. Note that there, if the white-light use power source 115 has not been turned on by the brightness detecting means 524, even if the switch 2 is depressed, the stimulating light is not emitted. That is to say, the stimulating light can only be emitted when the forward end portion of the endoscope insertion portion 100 is inside the body of a patient. After a measurement has been taken, the normal-image detecting state is switched to if the switch 2 is depressed. (Here, the voltage of the semiconductor-laser use power source is brought down to a predetermined voltage and is placed in a standby state, and the stimulating light is not emitted.) Then, the endoscope insertion portion 100 is removed from the body of the patient, however, at this time, when the endoscope insertion portion 100 has been removed, to a position it can be safely removed to, even with the white light off, the switch 3 is depressed and the white-light use power source is turned off. Alternatively, the white light can be reduced to a predetermined brightness. Subsequently, when the brightness of any of the pixels of the normal image is detected by the brightness detecting means 524 to be larger than a predetermined threshold value, the endoscope insertion portion 100 is recognized as being located outside the body of the patient and the brightness detecting means 524 outputs a detection signal to the stimulating light emission prevention controlling means 702. The stimulating light emission prevention controlling means 702 turns of the semiconductor-laser use power source 112, by use of the control computer 200, and prevents the emission of stimulating light.

According to the fluorescent endoscope apparatus of the configuration described above, a brightness detecting means is provided for detecting the brightness of a normal image, and when said brightness detecting means detects that any of the pixels of the normal image has a brightness larger than a predetermined threshold value, the forward end portion of the insertion portion is recognized as being located outside the body of the patient and the brightness detecting means outputs a detection signal to the stimulating light emission prevention controlling means, and because the stimulating light emission prevention controlling means prevents the emission of stimulating light, the safety of the patient and the operator can be ensured.

Figure 4:
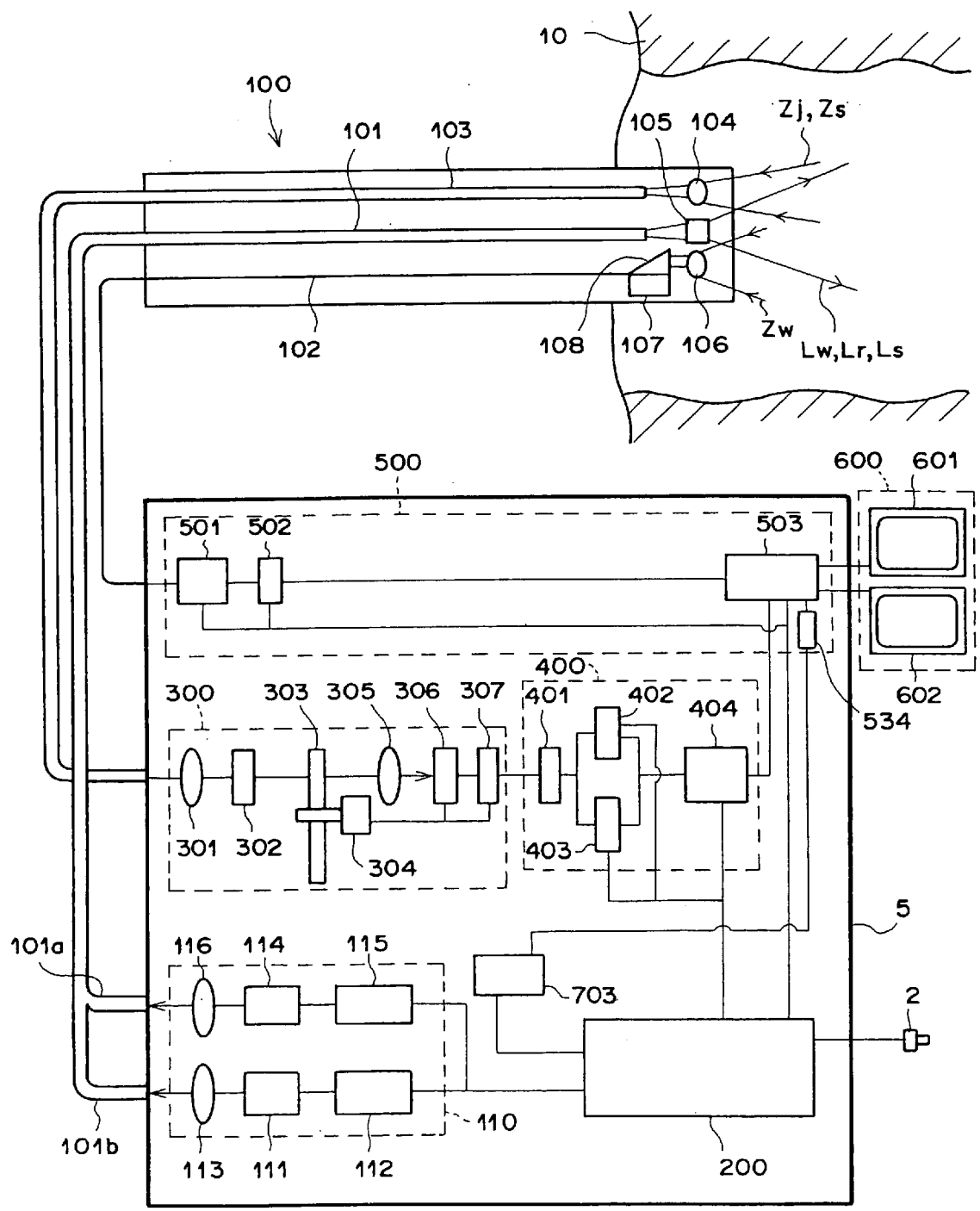
FIG. 4 is a schematic drawing of a fluorescent endoscope apparatus according to the fourth embodiment of the present invention.

Next, the fluorescent endoscope apparatus according fourth embodiment of the present invention will be explained. FIG. 4 is a schematic drawing of the configuration of a fluorescent endoscope apparatus according to the fourth embodiment of the present invention. Note that in so far as further explanation of the same elements occurring in the first embodiment is not particularly required, it has been omitted.

The fluorescent endoscope apparatus according to the fourth embodiment of the present invention comprises a color signal detecting means 534 for detecting the color signal of a normal image, and a white-light switch 3 for turning off the white-light use power source 115.

Next, the operation of the fluorescent endoscope apparatus according to the current embodiment will be explained. First, while in the normal-image displaying state, the endoscope insertion portion 100 is inserted into the body of a patient, and the color signal of each pixel occurring in a detected normal image, that is the RGB signal output from the video signal processing circuit 503, is detected by the color signal detecting means 534. After insertion, when the R signal component above a predetermined tone is above a predetermined threshold value, the color signal detecting means 534 sends a detection signal to stimulating light emission prevention controlling means 703, and the stimulating light emission prevention controlling means 703 put the stimulating light in the emission-capable state. (Note that here, the emission-capable state means that the semiconductor-laser use power source 112 is brought down to a predetermined voltage and the stimulating light emission is placed in a standby state.) Until this signal has been input to the stimulating light emission prevention controlling means 703, by turning the semiconductor-laser use power source 112 off, the stimulating light emission prevention controlling means 703 maintains the stimulating light in the emission-prohibited state. That is, it is possible for the stimulating light to be emitted only when the forward end portion of the endoscope insertion portion 100 is inside he body of a patient. Then, by depressing the switch 2, the semiconductor-laser use power source 112 is turned on and the stimulating light is emitted. Then, after a measurement has been taken, the normal-image detecting state is switched to by depressing the switch 2. (Note that here, the semiconductor-laser use power source 112 is in the standby state.) Subsequently, while in the normal-image displaying state, the endoscope insertion portion 100 is removed from the body of the patient, however, when the R signal component above a predetermined tone is below a predetermined threshold value, the endoscope insertion portion 100 is recognized as being located outside the body of the patient and the color signal detecting means 534 sends a detection signal to stimulating light emission prevention controlling means 703. The stimulating light emission prevention controlling means 703 turns the semiconductor-laser use power source 112 off, by use of the control computer 200, and prevents the emission of stimulating light.

Figure 5A:
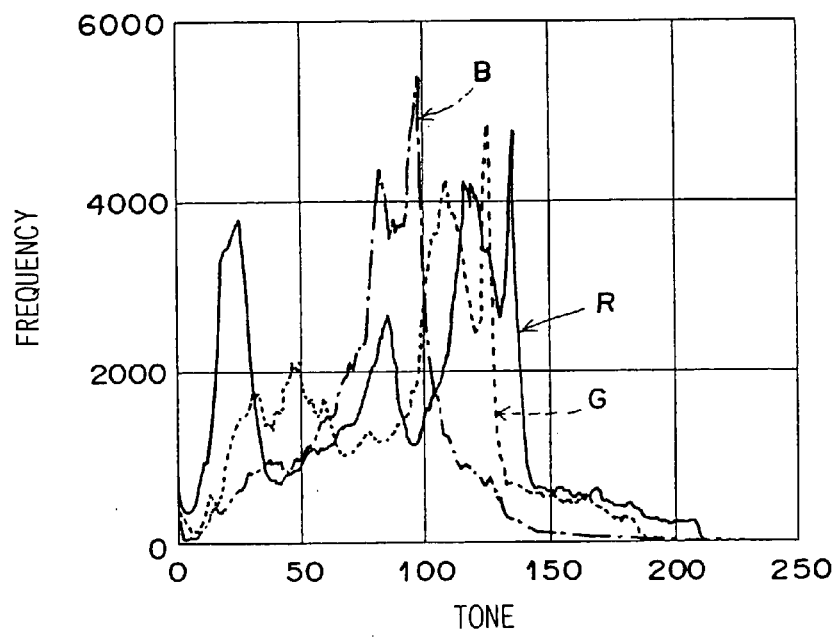
FIGS. 5A and 5B show a histogram of the RGB signal of a normal image of the background light of a diagnosis room and a histogram of the RGB signal of a normal image of a body cavity, respectively.
Figure 5B:
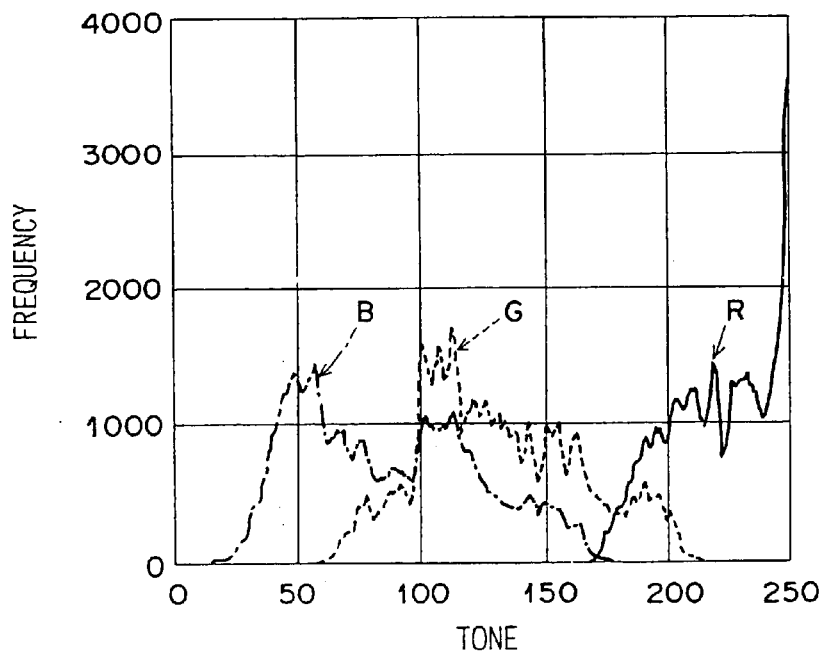

Note that the RGB signal distribution inside the body of a patient and the RGB signal distribution outside the body of a patient (the RGB signal distribution of the diagnosis room) occurring when a measurement is taken using the fluorescent endoscope apparatus are shown in FIG. 5. As shown in FIG. 5, the distribution of the R signal component occurring inside the body is distributed in the high-tone area, and the distribution of the G signal component and the B signal component is in a separated state. The RGB signal distribution occurring outside the body (the RGB signal distribution of the diagnosis room) is such that the R component, the G component and the B components are stacked on each other; clearly a different distribution from that of the RGB signal distribution occurring inside the body of a patient. The color signal detecting means 534 detects this difference in RGB signal distribution. For example., the number of pixels (frequency) of the an R signal component above a predetermined tone is computed, and when this computed value is below a predetermined threshold value, the forward end portion of the endoscope insertion portion can be determined as being outside the body of a patient.

According to the fluorescent endoscope apparatus of the configuration described above, a color signal detecting means is provided for detecting the color signal of a normal image, and when said color signal detecting means detects that the R signal component of the RGB signal of each of the pixels of the normal image is smaller than a predetermined threshold value, the forward end portion of the insertion portion is recognized as being located outside the body of the patient and the color signal detecting means outputs a detection signal to the stimulating light emission prevention controlling means, and because the stimulating light emission prevention controlling means prevents the emission of stimulating light, the stimulating light does not enter the eyes of the operator and cause injury thereto and safety can be ensured.

Figures 6, 7:
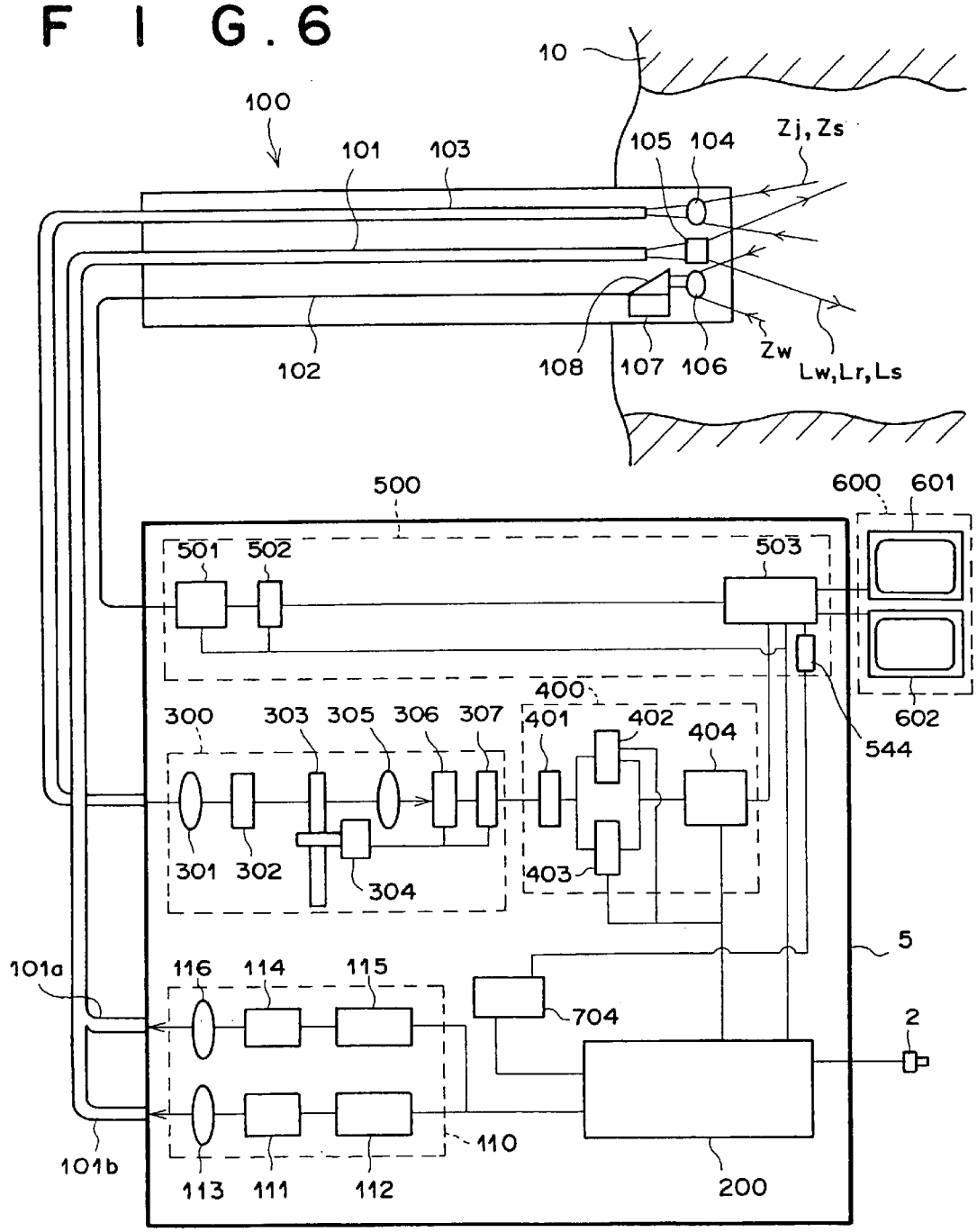
FIG. 6 is a schematic drawing of a fluorescent endoscope apparatus according to the fifth embodiment of the present invention.
FIG. 7 shows an image template formed of straight-line components.

Next, the fluorescent endoscope apparatus according fifth embodiment of the present invention will be explained. FIG. 6 is a schematic drawing of the configuration of a fluorescent endoscope apparatus according to the fifth embodiment of the present invention. Note that in so far as further explanation of the same elements occurring in the first embodiment is not particularly required, it has been omitted.

The fluorescent endoscope apparatus according to the fifth embodiment of the present invention comprises a straight-line detecting means 544 for detecting the straight-line pattern of a normal image.

Next, the operation of the fluorescent endoscope apparatus according to the current embodiment will be explained. First, while in the normal-image displaying state, the endoscope insertion portion 100 is inserted into the body of a patient, and the straight line detecting means subjects the digital data of a normal image -to a Hough transform and detects the straight-line component of the normal image. After insertion, when the number of straight lines contained in a normal image is less than a predetermined threshold value, the straight-line detecting means 544 sends a detection signal to stimulating light emission prevention controlling means 704, and the stimulating light emission prevention controlling means 704 put the stimulating light in the emission-capable state. (Note that here, the semiconductor-laser use power source 112 is in a stand by state.) Until this signal has been input to the stimulating light emission prevention controlling means 704, the stimulating light emission prevention controlling means 704 maintains the stimulating light in the emission-prohibited state. That is, it is possible for the stimulating light to be emitted only when the forward end portion of the endoscope insertion portion 100 is inside he body of a patient. Then, by depressing the switch 2, the semiconductor-laser use power source 112 is turned on and the stimulating light is emitted. Then, after a measurement has been taken, the normal-image detecting state is switched to by depressing the switch 2. (Note that here, the semiconductor-laser use power source 112 is in the standby state.) Subsequently, while in the normal-image displaying state, the endoscope insertion portion 100 is removed from the body of the patient, however, when the number of straight lines contained in a normal image is above a predetermined threshold value, the endoscope insertion portion 100 is recognized as being located outside the body of the patient and the straight-line detecting means 544 sends a detection signal to stimulating light emission prevention controlling means 704. The stimulating light emission prevention controlling means 704 turns the semiconductor-laser use power source 112 off, by use of the control computer 200, and prevents the emission of stimulating light.

According to the fluorescent endoscope apparatus of the configuration described above, a straight-line detecting means is provided for detecting the straight-line pattern of a normal image, and when the straight-line component of a normal image detected by said straight-line. detecting means is larger than a predetermined threshold value, the forward end portion of the insertion portion is recognized as being located outside the body of the patient and the straight-line detecting means outputs a detection signal to the stimulating light emission prevention controlling means, and because the stimulating light emission prevention controlling means prevents the emission of stimulating light, the stimulating light does not enter the eyes of the operator and cause injury thereto and safety can be ensured.

Note that aside from a straight-line detecting method employing image processing by a Hough transform, a method wherein an image template of only straight lines such as that shown in FIG. 7 is superposed on a normal image, whereby the straight-line component thereof is enhanced, and the straight-line component detected, can also be used.

Figure 8:
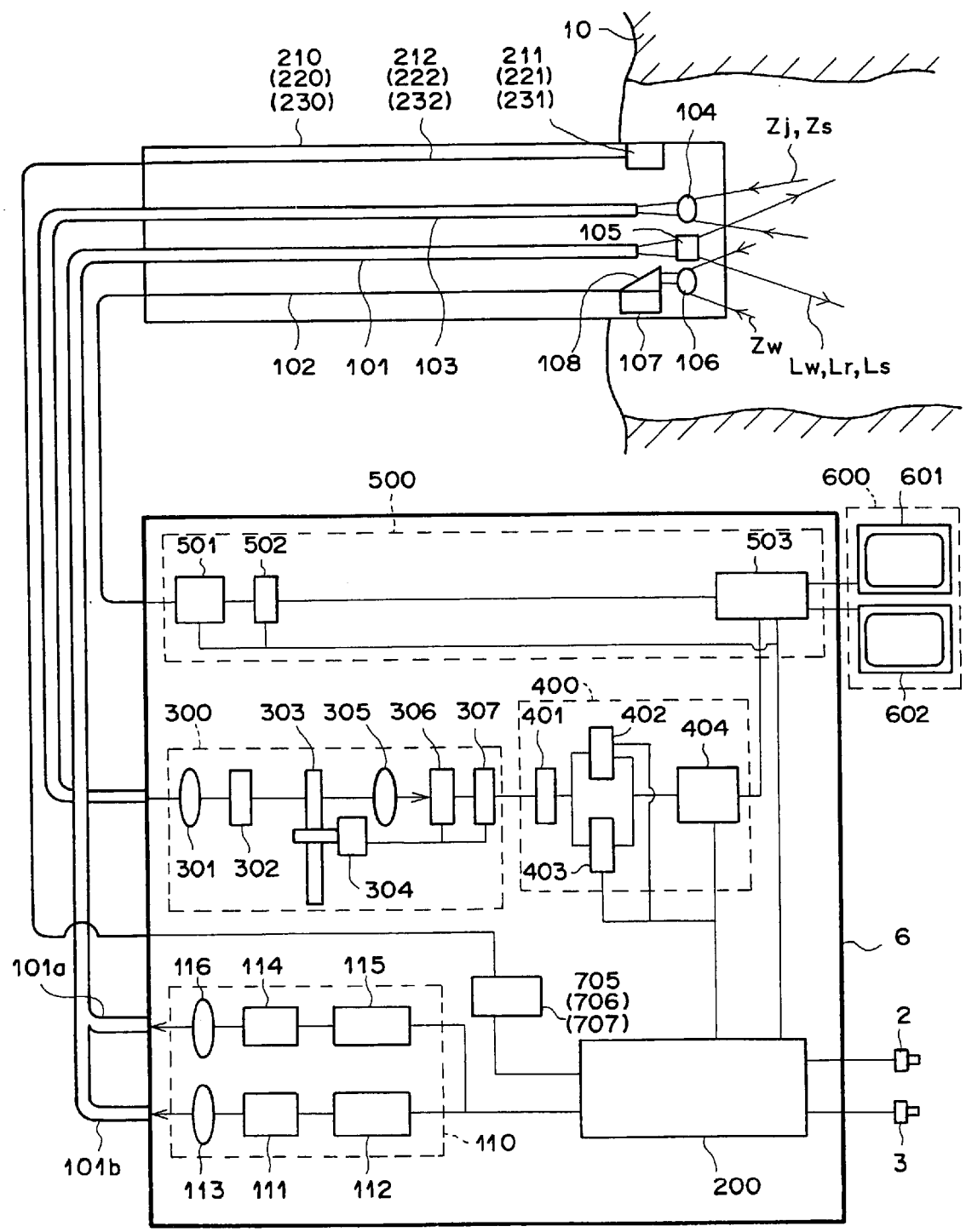
FIG. 8 is a schematic drawing of a fluorescent endoscope apparatus according to the sixth, seventh and eight embodiments of the present invention.

Next, the fluorescent endoscope apparatus according sixth embodiment of the present invention will be explained. FIG. 8 is a schematic drawing of the configuration of a fluorescent endoscope apparatus according to the sixth embodiment of the present invention. Note that in so far as further explanation of the same elements occurring in the first embodiment is not particularly required, it has been omitted.

The fluorescent endoscope apparatus according to the fourth embodiment of the present invention comprises a light strength detecting means 211 for detecting the light strength occurring near the forward end portion of the endoscope insertion portion 210 disposed in the forward end portion of the endoscope insertion portion 210, a detecting cable 212 for connecting said light strength. detecting means 211 and the stimulating light emission prevention controlling means 705, and a white-light switch 3 for turning the white-light use power source 115 off.

Next, the operation of the fluorescent endoscope apparatus according to the current embodiment will be explained. First, while in the white-light use power source 115 is in the off state, the endoscope insertion portion 210 is inserted into the body of a patient using the sight of the operator, and the light strength detecting means 211 detects the light strength occurring near t he forward end portion of the endoscope insertion portion 210. After insertion, if the light strength detected by the light strength detecting means 211 is below a predetermined threshold value, the light strength detecting means outputs a detection signal to the control computer 200, and the control computer 200 turns the white-light use power source on. Subsequently, the semiconductor-laser use power source is turned on by depressing the switch 2 and the stimulating light is emitted. Note that here, if the white-light use power source 115 has not been turned on by the light strength detecting means 211, even if the switch 2 is depressed, the stimulating light is not emitted. That is, it is only possible for the stimulating light to be emitted when the forward end portion of the endoscope insertion portion is inside the body of the patient. After a measurement has been taken, the normal-image detecting state is switched to by depressing the switch 2. (Note that here, the semiconductor-laser use power source 112 is in the standby state.) Subsequently, while in the normal-image displaying state, the endoscope insertion portion 210 is removed from the body of the patient, however, when the endoscope insertion portion is removed to a safe position where the removal may now be carried out safely even under the OFF state of the white light, the white-light use power source is turned off by depressing the white-light switch 3. Alternatively, the white light can be reduced to a predetermined brightness.

Subsequently, when the light strength detected by the light strength detecting means 211 is larger than a predetermined threshold value, the endoscope insertion portion 210 is recognized as being located outside the body of the patient and the light strength detecting means 211 sends a detection signal to stimulating light emission prevention controlling means 705. The stimulating light emission prevention controlling means 705 turns the semiconductor-laser use power source 112 off, by use of the control computer 200, and prevents the emission of stimulating light. Note that it is desirable that the light strength detecting means be disposed at a position several centimeters away from the forward end portion of the endoscope insertion portion.

According to the fluorescent endoscope apparatus of the configuration described above, a light strength detecting means is provided for detecting the light strength occurring near the forward end portion of the endoscope insertion potion, and when said light strength detecting means detects that light strength occurring near the forward end portion of the endoscope insertion portion is larger than a predetermined threshold value, the forward end portion of the insertion portion is recognized as being located outside the body of the patient and the light strength detecting means outputs a detection signal to the stimulating light emission prevention controlling means, and. because the stimulating light emission prevention controlling means prevents the emission of stimulating light, the stimulating light does not enter the eyes of the operator and cause injury thereto and safety can be ensured.

Next, the fluorescent endoscope apparatus according seventh embodiment of the present invention will be explained. Because the configuration of the fluorescent endoscope apparatus according to the seventh embodiment is substantially the same as that of the sixth embodiment shown in FIG. 8, only elements differing from the sixth embodiment are given element new reference numbers in FIG. 8. Note that in so far as further explanation of the same elements occurring in the first embodiment is not particularly required, it has been omitted.

The fluorescent endoscope apparatus according to the seventh embodiment of the present invention comprises a temperature detecting means 221 for detecting the temperature occurring near the forward end portion of the endoscope insertion portion 220 disposed in the forward end portion of the endoscope insertion portion 22.0, and a detecting cable 222 for connecting said temperature detecting means 221 and the stimulating light emission prevention controlling means 706.

Next, the operation of the fluorescent endoscope apparatus according to the current embodiment will be explained. The fluorescent endoscope apparatus according to the current embodiment is provided with a temperature detecting means 221 disposed in the forward end portion of the endoscope insertion portion 220, and when the temperature occurring near the forward end portion of the endoscope insertion portion is lower than 37° C. (the normal body temperature of a patient), the forward end portion of the endoscope insertion portion 220 is recognized as being located outside the body of the patient and the temperature detecting means 221 outputs a detection signal to stimulating light emission prevention controlling means 706. The stimulating light emission prevention controlling means 706 turns the semiconductor-laser use power source 112 off, by use of the control computer 200, and prevents the emission of stimulating light.

Note that it is desirable that the temperature detecting means employed in the fluorescent endoscope apparatus according to the current embodiment,is temperature detecting means capable of detecting a temperature of 37° C. at a high-speed response rate; such as a pyroelectric infrared detector, etc. For cases in which a pyroelectric infrared detector is used as the temperature detecting means; because the strength of the infrared rays emitted from the living-tissue subject is to be detected, it is best that the pyroelectric infrared detector be disposed at a position several centimeters away from the forward end portion of the endoscope insertion portion, and that the temperature to the side of the forward end portion of the endoscope insertion portion is detected. Further, aside from an infrared collector detecting means, a device for detecting the strength of the infrared radiation, the spectral distribution of the infrared radiation, or the strength of a particular wavelength range of infrared radiation, etc. can be used, or a the temperature can be computed from a combination of two or more of these data. Still further, it is desirable that the temperature detecting means is disposed at a position several centimeters away from the forward end portion of the endoscope insertion portion 220, and so that the temperature to the side of the forward end portion of the endoscope insertion portion 220 is detected.

According to the fluorescent endoscope apparatus of the configuration described above, a temperature detecting means is provided for detecting the temperature occurring near the forward end portion of the endoscope insertion potion, and when said temperature detecting means detects that the temperature occurring near the forward end portion of the endoscope insertion portion is below 37° C. (the normal body temperature of a patient), the forward end portion of the insertion portion is recognized as being located outside the body of the patient and the temperature detecting means outputs a detection signal to the stimulating light emission prevention controlling means, and because the stimulating light emission prevention controlling means prevents the emission of stimulating light, the stimulating light does not enter the eyes of the operator and cause injury thereto and safety can be ensured.

Next, the fluorescent endoscope apparatus according eighth embodiment of the present invention will be explained. Because the configuration of the fluorescent endoscope apparatus according to the eighth embodiment is substantially the same as that of the sixth embodiment shown in FIG. 8, only elements differing from the sixth embodiment are given new reference numbers in FIG. 6. Note that in so far as further explanation of the same elements occurring in the first embodiment is not particularly required, it has been omitted.

The fluorescent endoscope apparatus according to the eighth embodiment of the present invention is provided with a gas detecting means 231 for detecting components of the gas surrounding near the forward end portion of the endoscope insertion portion 230 disposed in the forward end portion of the endoscope insertion portion, and a detecting cable 232 for connecting said gas detecting means 231 and the stimulating light emission prevention controlling means 707.

Next, the operation of the fluorescent endoscope apparatus according to the current embodiment will be explained. The fluorescent endoscope apparatus according to the current embodiment is provided with a gas detecting means 231 disposed in the forward end portion of the endoscope insertion portion 230. When the density of the carbonic acid gas detected near the side of the forward tip of the endoscope insertion portion 230 by said gas detecting means 231 is smaller than a predetermined threshold value, the forward end portion of the endoscope insertion portion 230 is recognized as being located outside the body of the patient and the temperature detecting means 231 outputs a detection signal to the stimulating light emission prevention controlling means 707. The stimulating light emission prevention controlling means 707 turns the semiconductor-laser use power source 112 off, by use of the control computer 200, and prevents the emission of stimulating light. Further, it is desirable that the gas detecting means is disposed at a position several centimeters away from the forward end portion of the endoscope insertion portion 230, and so that the gas to the side of the forward end portion of the endoscope insertion portion 230 is detected.

Figure 9:
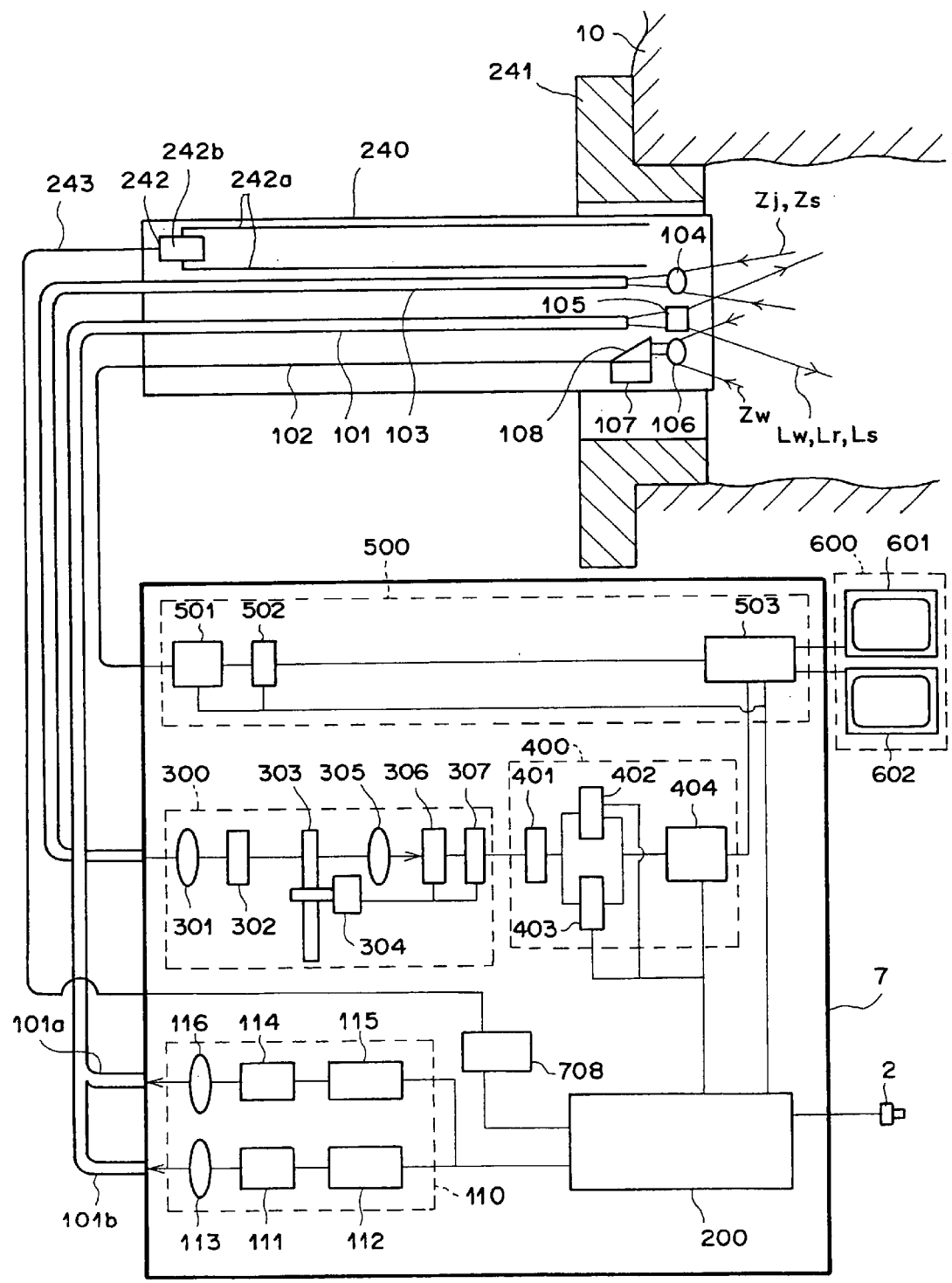
FIG. 9 is a schematic drawing of a fluorescent endoscope apparatus according to the ninth embodiment of the present invention.

According to the fluorescent endoscope apparatus of the configuration described above, a gas detecting means. is provided for detecting the gas occurring near the forward end portion of the endoscope insertion potion, and when said gas detecting means detects that the density of the carbonic acid gas occurring near the forward end,portion of the endoscope insertion portion is below a predetermined threshold value, the forward end portion of the insertion portion is recognized as being located outside the body of the patient and the temperature detecting means outputs a detection signal to the stimulating light emission prevention controlling means, and because the stimulating light emission prevention controlling means prevents the emission of stimulating light, the stimulating light does not enter the eyes of the operator and cause injury thereto and safety can be ensured. Next, the fluorescent endoscope apparatus according ninth embodiment of the present invention will be explained. FIG. 9 is a schematic drawing of the configuration of a fluorescent endoscope apparatus according to the ninth embodiment of the present invention. Note that in so far as further explanation of the same elements occurring in the first embodiment is not particularly required, it has been omitted.

The fluorescent endoscope apparatus according to the eighth embodiment of the present invention is provided with a magnetic field producing means 241, which is mounted at the opening of the body orifice of the patient into which the endoscope insertion portion is to be inserted, for producing a magnetic field, a magnetic field detecting means 242 for detecting the magnetic field produced within the endoscope insertion portion 240 by the magnetic field producing means 241, and a detecting cable 243 for connecting said magnetic field detecting means 242 and the stimulating light emission prevention controlling means 708. The magnetic field detecting means 242 is provided with a hole sensor 242*b* which is disposed around the entire circumference of the endoscope insertion portion and is formed of a wire 242*a* and a wire 242*a* formed of a material having a low permeability, for detecting magnetic flux.

Next, the operation of the fluorescent endoscope apparatus according to the current embodiment will be explained. The fluorescent endoscope apparatus according to the current embodiment is provided with a magnetic field producing means 241, which is mounted at the entrance to the body orifice into which the endoscope insertion portion is to be inserted, for producing a magnetic field, and a magnetic field detecting means 242 disposed inside the endoscope insertion portion 240 for detecting said magnetic field. When the forward end portion of the endoscope insertion portion 240 is brought near the magnetic field producing means 242 mounted at the opening of the body orifice into which it is inserted, the hole sensor 242*b* detects the magnetic field produced by the magnetic field producing means 242 as a change in the magnetic flux of the wire 242*a* and outputs a detection signal to the stimulating light emission prevention controlling means 708. Then, when this magnetic field produced by the magnetic field producing means 241 is not detected by the magnetic field detecting means 242, the forward end portion of the endoscope insertion portion 240 is recognized as being located outside the body of the patient and the stimulating light emission prevention controlling means 708 turns the semiconductor-laser use power source 112 off, by use of the control computer 200, and prevents the emission of stimulating light. Note that because the wire 242*a* of the magnetic field detecting means is disposed around the entire circumference of the endoscope insertion portion 240, when the endoscope insertion portion 240 is inside the body of the patient, the stimulating light is in the emission-capable state. Further, the magnetic field producing means can be housed in the mouthpiece mounted at the opening of the body orifice of the patient into which the endoscope insertion portion is inserted. Still further, it is desirable that a portion of the endoscope insertion portion is removed, and the magnetic field detecting means 242 is disposed around the entire circumference of the endoscope insertion portion (preferable several centimeters away from the forward end portion of the endoscope insertion portion).

According to the fluorescent endoscope apparatus of the configuration described above, a magnetic field producing means, which is mounted at the entrance to the body orifice into which the endoscope insertion portion is to be inserted, for producing a magnetic field, and a magnetic field detecting means disposed inside the endoscope insertion portion for detecting said magnetic field are provided; based on the detection by the magnetic field detecting means of a magnetic field produced by the magnetic field producing means, the forward end portion of the insertion portion is recognized as being located outside the body of the patient and the magnetic field detecting means outputs a detection signal to the stimulating light emission prevention controlling means, and because the stimulating light emission prevention controlling means prevents the emission of stimulating light, the stimulating light does not enter the eyes of the operator and cause injury thereto and safety can be ensured.

Figure 10:
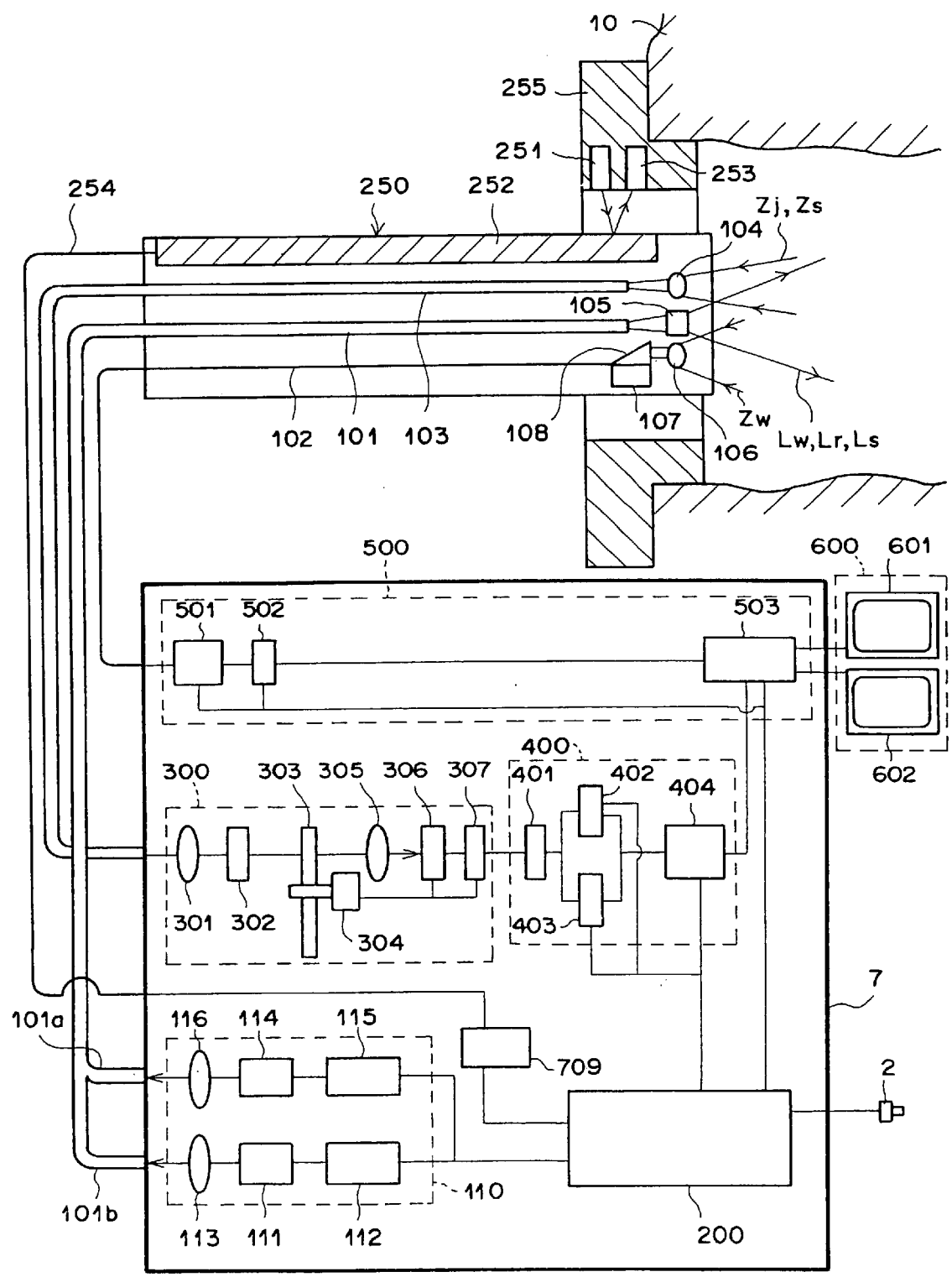
FIG. 10 is a schematic drawing of a fluorescent endoscope apparatus according to the tenth embodiment of the present invention.

Next, the fluorescent endoscope apparatus according tenth embodiment of the present invention will be explained. FIG. 10 is a schematic drawing of the configuration of a fluorescent endoscope apparatus according to the tenth embodiment of the present invention. Note that in so far as further explanation of the same elements occurring in the first embodiment is not particularly required, it has been omitted.

The fluorescent endoscope apparatus according to the tenth embodiment of the present invention is provided with an insertion opening mount 255 mounted at the opening of the body orifice of the patient into which the endoscope insertion portion is inserted, a light emitting means 251 housed within the insertion opening mount 255, a reflecting means 252 disposed within the endoscope insertion portion 250 for reflecting the light emitted from the light emitting means 251, a reflected-light detecting means 253 housed within the insertion opening mount 255 for detecting the reflected light reflected by the reflecting means 252, and a detecting cable 254 for connecting the reflected-light detecting means 253 and the stimulating light emission prevention controlling means 709 disposed within the image signal processing portion. The reflecting means is disposed around the entire circumference of the endoscope insertion portion, and is a film made of a material having a high reflectivity ratio.

Next, the operation of the fluorescent endoscope apparatus according to the current embodiment will be explained. The fluorescent endoscope apparatus according to the current embodiment is provided with a light emitting means 251 for emitting light at the opening of the body orifice into which the endoscope insertion portion is inserted, a reflecting means 252 for reflecting the light emitted from the light emitting means 251, and a reflected-light detecting means 253 for detecting the reflected light reflected by the reflecting means 252. When the forward end portion of the endoscope insertion portion is brought near the light emitting means 251 at the opening of the body orifice into which the endoscope insertion portion 250 is inserted, the light emitted from the light emitting means 251 is reflected by the reflecting means 252 disposed on the endoscope insertion portion, and the reflected light is detected by the reflected-light detecting means 253 and the reflected-light detecting means outputs a signal to the stimulating light emission prevention controlling means 709. Then, when the reflected light reflected from the reflecting means 252 is not detected by the reflected-light detecting means 242, the forward end portion of the endoscope insertion portion 250 is recognized as being located outside the body of the patient and the stimulating light emission prevention controlling means 709 turns the semiconductor-laser use power source 112 off, by use of the control computer 200, and prevents the emission of stimulating light. Note that because the reflecting means 252 is disposed around the entire circumference of the endoscope insertion portion 250, when the endoscope insertion portion 250 is inside the body of the patient, the stimulating light is in the emission-capable state. Further, the endoscope insertion portion 250 is inserted into the body of a patient in a manner that the light emitted from the light emitting means 251 always irradiates the reflecting means 252. Still further, if the material of the outer circumference wall of the endoscope insertion portion 250 has a reflectivity ratio the same as that of the reflecting means 252, the reflecting means 252 is not particularly necessary. Further still, it is desirable that a portion of the endoscope insertion portion is removed, and the reflecting means 252 is disposed around the entire circumference of the endoscope insertion portion (preferable several centimeters away from the forward end portion of the endoscope insertion portion).

According to the fluorescent endoscope apparatus of the configuration described above, a light emitting means mounted at the opening of the body orifice into which the endoscope insertion portion is inserted and a reflected-light detecting means for detecting the reflected light reflected by the endoscope insertion portion upon irradiation thereof by the light emitted by the light emitting means are provided; based on the detection by the reflected-light detecting means of reflected light, the forward end portion of the insertion portion is recognized as being located outside the body of the patient and the reflected-light detecting means outputs a detection signal to the stimulating light emission prevention controlling means, and because the stimulating light emission prevention controlling means prevents the emission of stimulating light, the stimulating light does not enter the eyes of the operator and cause injury thereto and safety can be ensured.

Figure 11:
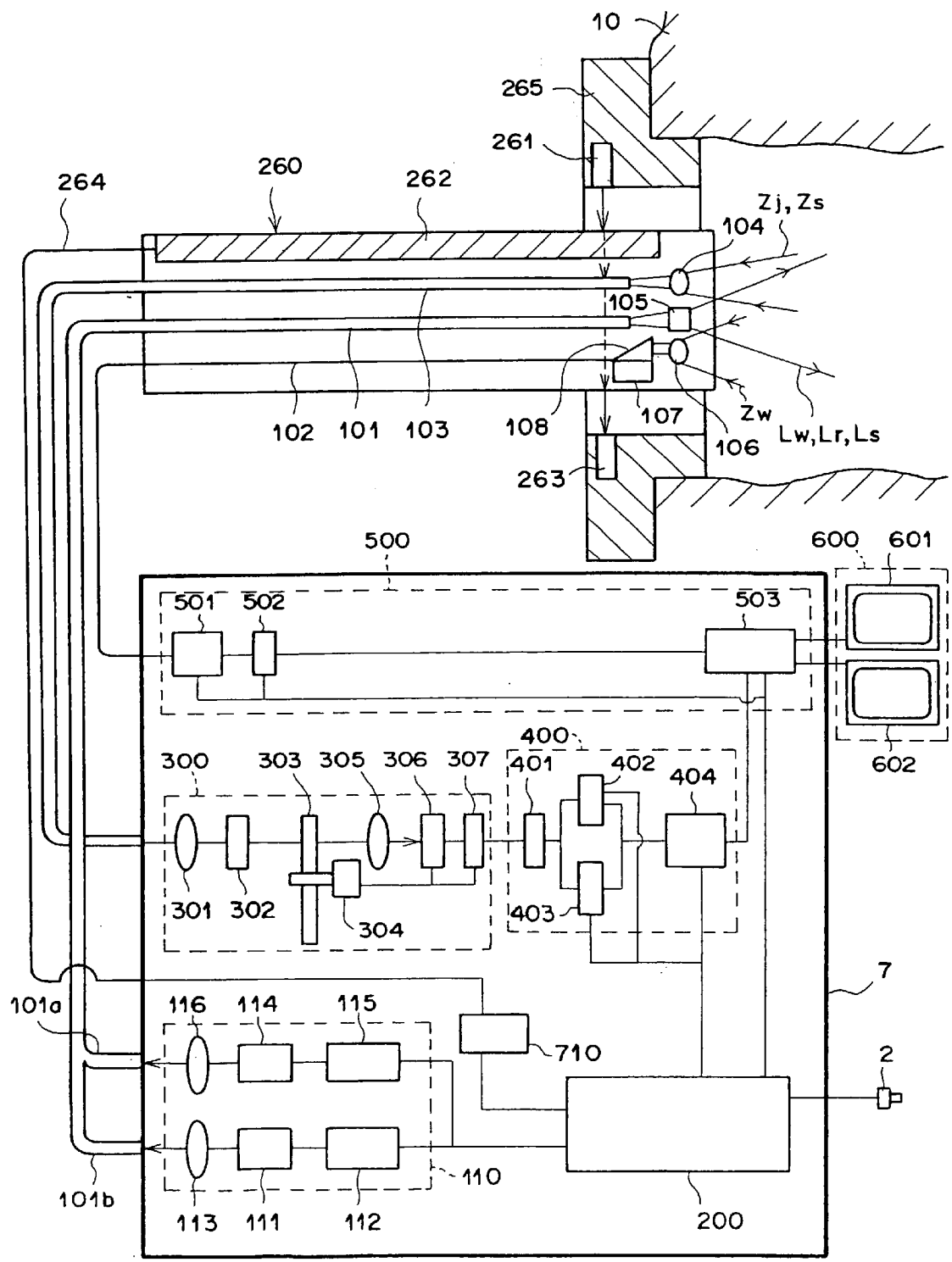
FIG. 11 is a schematic drawing of a fluorescent endoscope apparatus according to the eleventh embodiment of the present invention.

Next, the fluorescent endoscope apparatus according eleventh embodiment of the present invention will be explained. FIG. 11 is a schematic drawing of the configuration of a fluorescent endoscope apparatus according to the eleventh embodiment of the present invention. Note that in so far as further explanation of the same elements occurring in the first embodiment is not particularly required, it has been omitted.

The fluorescent endoscope apparatus according to the eleventh embodiment of the present invention is provided with an insertion opening mount 265 mounted at the opening of the body orifice of the patient into which the endoscope insertion portion is inserted, a light emitting means 261 housed within the insertion opening mount 265, a light-transmitting means 252 disposed within the endoscope insertion portion 260 for transmitting at a predetermined light-transmission rate the light emitted from the light emitting means 261, a transmitted-light detecting means 263 housed within the insertion opening mount 265 for detecting the reflected light transmitted by the endoscope insertion portion 260 containing the light-transmitting means 262, and a detecting cable 264 for connecting the transmitted-light detecting means 263 and the stimulating light emission prevention controlling means 710 disposed within the image signal processing portion. The light-transmitting means is disposed throughout the endoscope insertion portion, and is a film made of a material having a predetermined light-transmission ratio.

Next, the operation of the fluorescent endoscope apparatus according to the current embodiment will be explained. The fluorescent endoscope apparatus according to the current embodiment is provided with a light emitting means 261 for emitting light at the opening of the body orifice into which the endoscope insertion portion is inserted, a light transmitting means 262, which is disposed throughout the endoscope insertion portion, for, transmitting the light emitted from the light emitting means 261, and a transmitted-light detecting means 263 for detecting the reflected light reflected by the light transmitting means 262. When the strength of the transmitted light detected by the transmitted-light detecting means 263 is above a predetermined threshold value, the forward end portion of the endoscope insertion portion 250 is recognized as being located outside the body of the patient, and the transmitted-light detecting means 263 outputs a detection signal to the stimulating light emission prevention controlling means 710. The stimulating light emission prevention controlling means 710 turns the semiconductor-laser use power source 112 off, by use of the control computer 200, and prevents the emission of stimulating light. Note that the light transmitted by the light transmitting means 262 having a predetermined light-transmission rate is such that it is of a strength making it distinguishable from the transmitted light that is transmitted through the endoscope., insertion portion but is not transmitted through the light-transmitting means 262. Further, because the light-transmitting means 262 is disposed around the entire circumference of the endoscope insertion portion 260, when the endoscope insertion portion 260 is inside the body of the patient, the stimulating light is in the emission-capable state.

Further, the endoscope insertion portion is inserted into the body of a patient in a manner that the light emitted from the light emitting means 261 is always irradiating the light-transmitting means 262. Still further, if the material of the outer circumference wall of, the endoscope insertion portion 260 has a light-transmission ratio the same as that of the light-transmitting means 262, the light-transmitting means 262 is not particularly necessary. Further still, it is desirable that a portion of the endoscope insertion portion is removed, and the light-transmitting means 262 is disposed around the entire circumference of the endoscope insertion portion (preferable several centimeters away from the forward end portion of the endoscope insertion portion).

According to the fluorescent endoscope apparatus of the configuration described above, a light emitting means mounted at the opening of the body orifice. into which the endoscope insertion portion is inserted and a transmitted-light detecting means for detecting the transmitted light transmitted by the endoscope insertion portion upon irradiation thereof by the light emitted from the light emitting means are provided; based on the detection by the transmitted-light detecting means of transmitted light, the forward end portion of the insertion portion is recognized as being located outside the body of the patient and the transmitted-light detecting means outputs a detection signal to the stimulating light emission prevention controlling means, and because the stimulating light emission prevention controlling means prevents the emission of stimulating light, the stimulating light does not enter the eyes of the operator and cause injury thereto and safety can be ensured.

Next, the fluorescent endoscope apparatus according twelfth embodiment of the present invention will be explained. FIG. 12 is a schematic drawing of, the configuration of a fluorescent endoscope apparatus according to the twelfth embodiment of the present invention. Note that in so far as further explanation of the same elements occurring in the first embodiment is not particularly required, it has been omitted.

The fluorescent endoscope apparatus according to the twelfth embodiment of the present invention is provided with an airspace volume detecting means 270 for detecting the airspace volume C occurring between the endoscope insertion portion 270 and the body of the patient, a pressure means disposed within the endoscope insertion portion 270 for keeping the pressure of the endoscope insertion portion 270 at a uniform level, and a detecting cable for connecting the pressure means 272 and the airspace volume detecting means of the image signal processing portion. The pressure means 272 is disposed around the entire circumference of the endoscope insertion portion, and so that the pressure of the endoscope insertion portion is made to be of a uniform value.

Next, the operation of the fluorescent endoscope apparatus according to the current embodiment will be explained. The fluorescent endoscope apparatus according to the current embodiment is provided with an airspace volume detecting means 271, which is disposed within the image signal processing portion, for detecting the airspace volume C between the endoscope insertion portion 270 and the body of a patient, and a pressure means 272, which is disposed around the entire circumference of the endoscope insertion portion, for making the pressure of the endoscope insertion portion to be of a uniform value, wherein the airspace volume detecting means is provided with an alternating current power source through which a high-frequency current flows (not shown) .This high-frequency current flows through the detecting cable 273 to the pressure means 272 of the endoscope insertion portion, and through the airspace volume C between the endoscope insertion portion and the body of the patient to the body of the patient. The airspace volume detecting means 271 and the body of the patient are grounded and connected by a ground cable (not shown)

The airspace volume detecting means 271 detects the pressure of the pressure means 272 disposed within the endoscope insertion portion, by causing the high-frequency current to flow, the airspace volume C between the pressure means 272 and the body of the patient, and the pressure due to the pressure of the body of the patient. When the endoscope insertion portion 270 is inside the body of the patient, the pressure detected by the airspace volume detecting means 271 is of a uniform value. Then, when the pressure detected by the airspace volume detecting means 271 is above a predetermined threshold value, the forward end portion of the endoscope insertion portion 250 is recognized as being located outside the body of the patient, and the airspace volume detecting means 271 outputs a detection signal to the stimulating light emission prevention controlling means 711. The stimulating light emission prevention controlling means 711 turns the semiconductor-laser use power source 112 off, by use of the control computer 200, and prevents the emission of stimulating light. Note that if the material of which the endoscope insertion portion is formed is the same as that of the pressure means 272, it is not particularly necessary to provide a separate pressure means.

According to the fluorescent endoscope apparatus of the configuration described above, an airspace volume detecting means is provided, and when the airspace volume detected is larger than a predetermined threshold value, the forward end portion of the insertion portion is recognized as being located outside the body of the patient and the airspace volume detecting means outputs a detection signal to the stimulating light emission prevention controlling means, and because the stimulating light emission prevention controlling means prevents the emission of stimulating light, the stimulating light does not enter the eyes of the operator and cause injury thereto and safety can be ensured.

According to the fluorescent endoscope apparatuses of each of the embodiments described above, the stimulating light emission prevention controlling means has carried out the prevention of the emission of stimulating light by the output of a control signal from a control computer, however, the stimulating light can also be prevented from being emitted by placing a shutter or the like in the optical path through which the stimulating light is guided.

Figure 13:
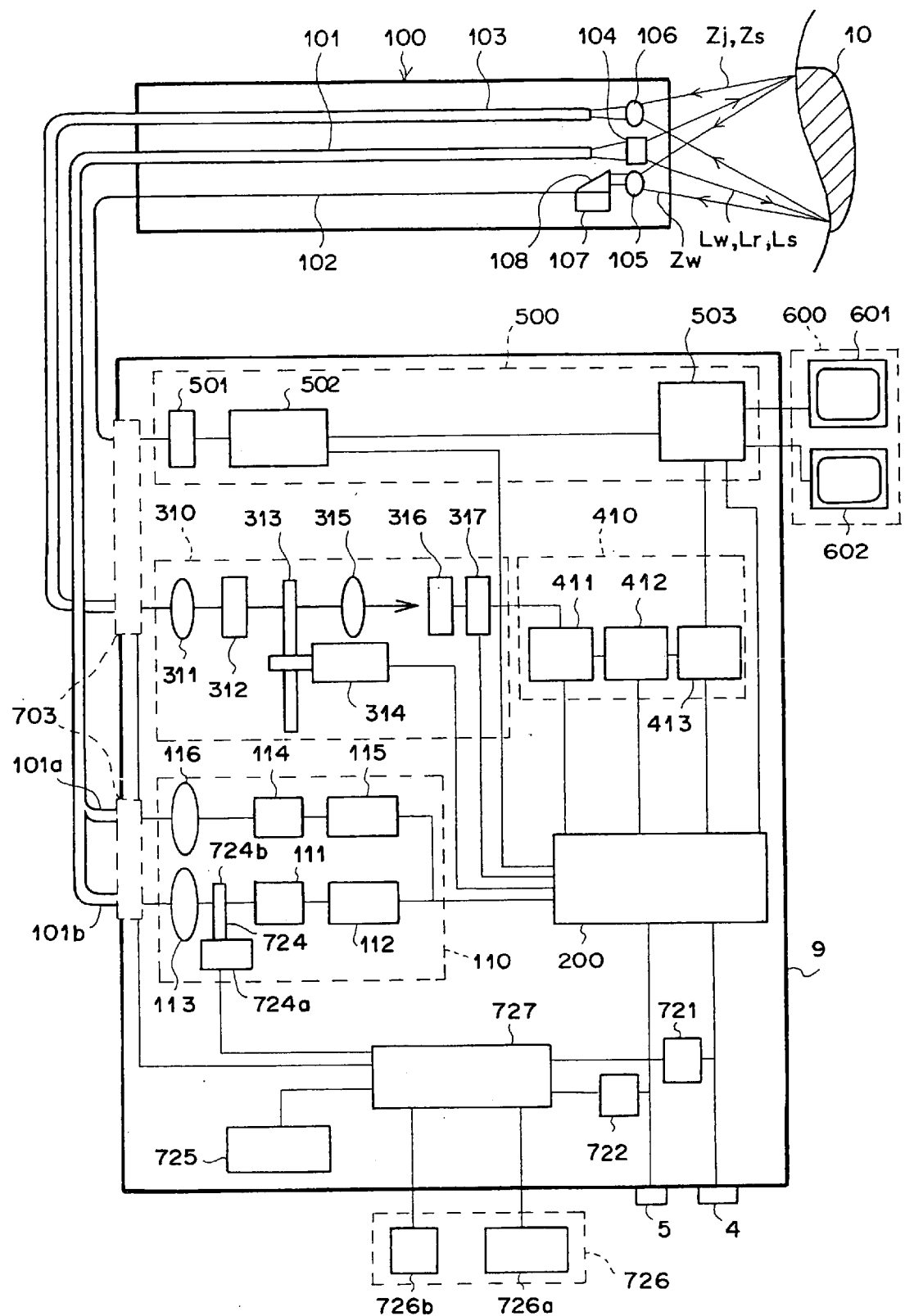
FIG. 13 is a schematic drawing of a fluorescent endoscope apparatus according to the thirteenth embodiment of the present invention.
Figure 14:
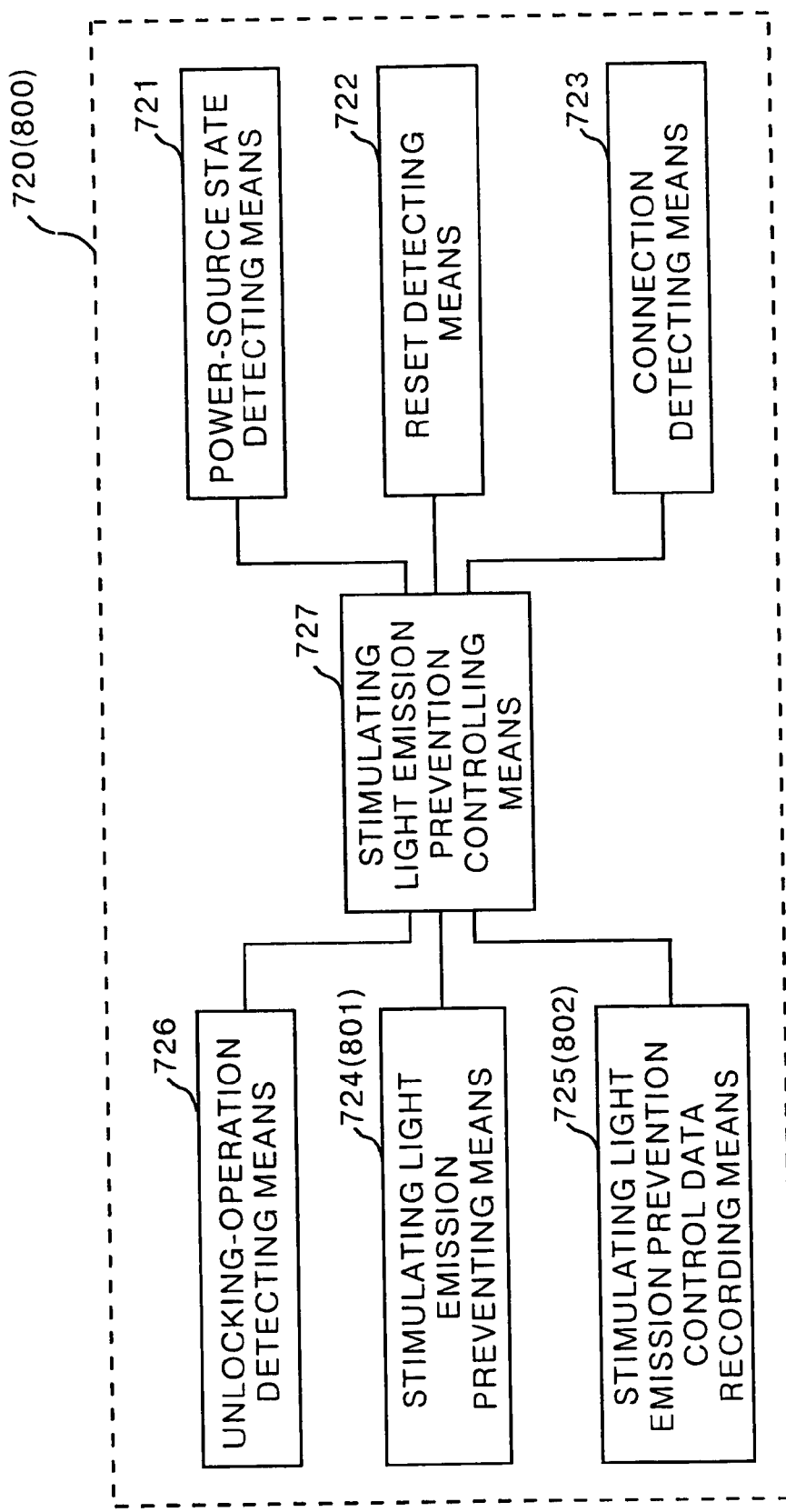
FIG. 14 is a schematic drawing of the stimulating light emission prevention control unit utilized in the fluorescent endoscope apparatuses according to the thirteenth and fourteenth embodiments of the present invention.

Next, the fluorescent endoscope apparatus according thirteenth embodiment of the present invention will be explained. FIGS. 13 and 14 are schematic drawings of the configuration of a fluorescent endoscope apparatus according to the thirteenth embodiment of the present invention. Note that in so far as further explanation of the same elements occurring in the first embodiment is not particularly required, it has been omitted.

The fluorescent endoscope apparatus according to the twelfth embodiment of the present invention comprises an image processing portion 9, which is provided with an illuminating unit 110 provided with two light sources for emitting normal-image use white light Lw and autofluorescent-light image use stimulating light Lr, respectively, an image detecting unit 310 for detecting an autofluorescent-light image Zj emitted from a living-tissue subject 10 upon irradiation thereof by the stimulating light Lr, and for digitizing said detected autofluorescent-light image Zj and outputting two-dimensional image signal thereof, an image computing unit 410 for computing the distance correction, etc. from the two-dimensional image data output from the image detecting unit 310 and computing a computed image, and for comparing the data of each pixel of the computed image to recorded standard values and outputting a signal corresponding to the results of the comparison, a, display signal processing unit 500 for converting said two-dimensional image data and the signal output from the image computing unit 410 to a video signal, a stimulating light controlling unit 720 for putting the stimulating light in the emission-prohibited state when the system is turned on or reset, for unlocking the emission-prohibited state of the stimulating light when a measurement is to be taken or maintenance is to be performed, and for putting the stimulating light in the emission-prohibited state while a measurement is being taken or when the endoscope insertion portion 100 has been removed from the image signal processing portion while maintenance is being performed, a control-use; computer 200 connected to each unit for controlling the operation timing thereof, and a monitor unit 600 for displaying as a visible image the signal processed by the display signal processing unit 500.

The illuminating unit 110 is provided with a white light source 114 for emitting the normal-image use white light Lw and a white-light use power source 115 electrically connected to the white light source 114, a white-light use focusing lens 116 for focusing the white light emitted from the white light source 114, a GaN type semiconductor laser 111 for emitting the autofluorescent- light image use stimulating light Lr and a semiconductor-laser use power source 112 electrically connected to the GaN type semiconductor laser 111, and a stimulating-light use focusing lens 113 for focusing the white light emitted from the GaN type semiconductor laser 111.

The image computing means 310 is connected to an image fiber 103, and is provided with a fluorescent-image use collimator for guiding the autofluorescent-light image conveyed by the image fiber 103 to the focusing optical system, a stimulating light cutoff filter 312 for cutting off from the autofluorescent-light image the wavelengths of light close to that of the stimulating light, an optical transmitting filter 313 for extracting the desired wavelengths of light from the autofluorescent-light image passing through the cutoff filter 312, a filter rotating apparatus 314 for rotating said optical transmitting filter 313, a fluorescent-light use focusing lens 315 for focusing the autofluorescent-light image passing through optical transmitting filter 313, a fluorescent-image use high sensitivity detecting element 316 for detecting the autofluorescent-light image, and an AD converter 317 for digitizing the autofluorescent-light image detected by said fluorescent-image use high sensitivity detecting element 316 and outputting the digitized value as a two-dimensional image data.

Figure 15:
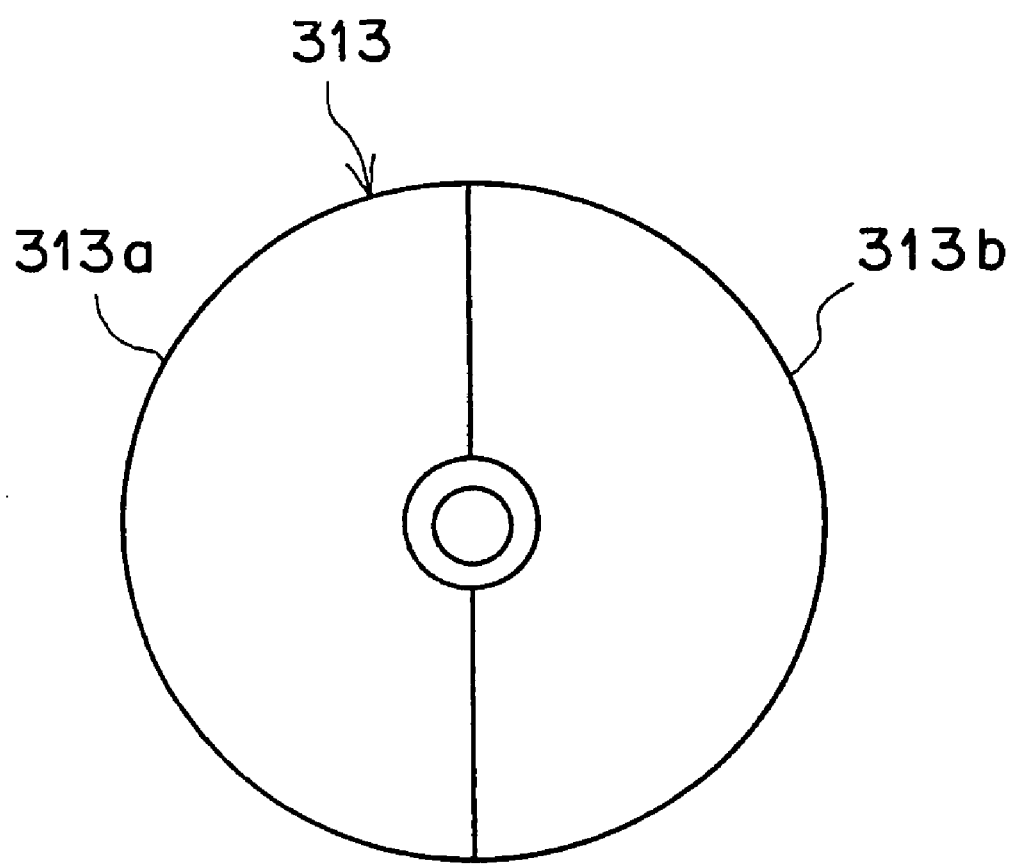
FIG. 15 is a schematic drawing of the optical transmitting filter utilized in the fluorescent endoscope apparatuses according to the thirteenth and fourteenth embodiments of the present invention.

As shown in FIG. 15, the optical transmitting filter 313 comprises two types of optical filters 313a and 313b. Optical filter 313a transmits light in the wavelength range of 430 nm to 730 nm, and optical filter 303b transmits light in the wavelength range of 430 nm to 530 nm.

The image computing unit 410 comprises an image data memory 411 for remembering the digitized autofluorescent-light image data, an inter-image image computing portion 412 for computing each pixel value based on each ratio between pixel values of the two autofluorescent-light images, which are formed of two different wavelength bands, respectively, that have been remembered in the memory 411, and an image comparing portion 413 for comparing each pixel value output from the inter-image image computing portion 412 to a standard value RE, which is recorded in the image comparing portion 413, and forming and outputting a computed image corresponding to the comparison result.

The standard value RE is a value set based on the pixel data of each pixel of an autofluorescent-light image of a living-tissue subject in which the normal tissue and the diseased tissue are clearly distinguishable.

The image signal processing unit 500 comprises an AD converter 501 for digitizing the visible image signal obtained by the normal image detecting element 107, a normal-image use memory 502 for storing the digitized normal image signal, and a video signal processing circuit 503 for converting the image signal output from the normal-image use memory 502 and the computed image of the image comparing portion 413 to a video signal.

The monitor unit 600 comprises a normal-image use monitor 601 and a computed image use monitor 602.

The stimulating light controlling unit 720, as shown in FIG. 14, comprises a power-source state detecting portion 722 for detecting that the power to the fluorescent image detecting apparatus has been switched from off to on, a reset detecting portion 722 for detecting that the fluorescent image detecting apparatus has been reset, a connection detecting means 723 for detecting that the endoscope insertion portion 100 has been disconnected, a stimulating light cutoff means 724 formed of an electromagnetic valve 724a and a shutter 724a for putting the stimulating light in the emission-prohibited state, a stimulating light emission prevention control data recording means 725 formed of a flash memory for recording the control data for controlling the stimulating light cutoff means 724, an unlocking operation detecting means 726 formed of an input operation detecting means 726a and a foot switch 726b, which have been provided as an input operation portion (not shown) for detecting the input operation for unlocking the emission-prohibited state of the stimulating light, and a stimulating light emission prevention control portion 727 for detecting the detection data from the power-source state detecting portion 721, the reset detecting portion 722, and the connection detecting portion, 723, for reading in the stimulating light emission prevention control data from the stimulating light emission control data recording means 725, and for unlocking the emission-prohibited state of the stimulating light, by the detection data from the unlocking operation detecting means 726.

Next, the operation of the fluorescent endoscope apparatus of the configuration described above according to the current embodiment will be explained.

First, an explanation will be given of the operation for when the system is turned on or reset. When the fluorescent endoscope apparatus is turned on, the power-source state detecting means 721 detects that,the power source has been switched from off to on, and data indicative thereof is sent to the stimulating light emission prevention control portion 727. The stimulating light emission prevention control portion 727 reads in the control data from the stimulating light emission control data recording means 725, controls the simulating light cutoff means 724, and puts the simulating light in the emission-prohibited state by forcing, by use of the electromagnetic valve 724a the shutter 724a to enter between the GaN type semiconductor laser 111 and the stimulating light guide 101b. Further, when the system is reset, that the fluorescent image detecting apparatus has been reset is detected by the reset detecting portion 722, and data indicative thereof is sent to the stimulating light emission prevention control portion 727. After this, the operation is the same as for when the system is turned on and the stimulating light is put in the emission-prohibited state.

Next, the operation for when an operation to take a measurement are initiated will be explained. When an operation to take a measurement is initiated, if the patient data is entered into the input portion the input operation is detected, and by the display of a normal image, the endoscope insertion portion is inserted into the opening of a body orifice of the patient. After confirming the normal image of the section of which a measurement is to be taken, by depressing the foot witch 726b, the stimulating light emission prevention control portion 727 controls the stimulating light cutoff means 724 and the shutter 724a is removed by the electromagnetic valve 724a, and the stimulating light is put in the emission-capable state, whereby it becomes possible to take a measurement. The detailed operations for when a normal image and a computed image are to be displayed are described below.

Next, the operation for when successive measurements are to be taken of different patients will be explained. When a measurement is to be taken of a different patient, in order to replace or clean the endoscope insertion portion 100, it is mandatory that the endoscope portion be removed from the image processing portion 9. When the endoscope insertion portion is removed from the image processing portion 9, that the endoscope insertion portion has been removed is detected by the connection detecting portion 723, and data indicative thereof is sent to the stimulating light emission prevention control portion 727. After this, the stimulating light is put in the emission-prohibited state in the same way as in the operation for when the system is turned on or reset, and also, by performing the same unlocking operation, taking a measurement again becomes possible.

Next the operation for when maintenance is to be initiated will be explained. When maintenance is initiated, in the same way as for when operations to take a measurement are initiated, the patient data is input to the input portion and the input operation is detected. However, the patient data entered at this time is pseudo patient data. Then, by the display of a normal image, the endoscope insertion portion is inserted into a body orifice of the patient. After confirming the normal image of the target tissue, by depressing the foot switch 726b, the stimulating light emission prevention control portion 727 controls the stimulating light cutoff means 724 and the shutter 724a is removed by the electromagnetic valve 724a, and the stimulating light is put in the. emission-capable state, whereby it becomes possible to perform maintenance operations requiring the emission of stimulating light.

Note that when maintenance is performed it is not mandatory that the endoscope insertion portion 100 be used; when maintenance employing the stimulating light is performed without using the endoscope insertion portion 100, by plugging a pseudo endoscope insertion portion into the image processing portion 9 instead of the endoscope insertion portion 100, the stimulating light does not move to the emission-prohibited state.

Next, the operation for when a computed image is to be displayed will be explained. To display a computed image, the semiconductor-laser use power source is activated based on a signal from the control-use computer 200, and stimulating light Lr having a wavelength of 410 nm is emitted from the GaN type semiconductor laser 111 The stimulating light Lr is transmitted by the stimulating-light use focusing lens 113 and enters the stimulating-light guide 101b, and after being guided to the forward end portion of the endoscope insertion portion 100, it is emitted onto the living-tissue subject 10 from the illuminating lens 104.

The autofluorescent-light image emitted from the living-tissue subject 10 upon irradiation thereof by the stimulating light Lr is focused by the focusing lens 106 and enters the end portion of the image fiber 103, and passes through the image fiber 103 and enters the stimulating-light cutoff filter 312.

The autofluorescent-light image passing through the stimulating-light cutoff filter 312 enters the optical transmitting filter 313. Note that the stimulating-light cutoff filter 312 is a long-pass filter that transmits all wavelengths above 420 nm. Because the wavelength of the stimulating light Lr is 410 nm, it is cutoff by the stimulating-light cutoff filter 312 and does not enter the optical transmitting filter 313.

The filter rotating apparatus 314 is activated by the control-use computer 200, and after the autofluorescent-light image Zj passes through the optical filter 313a and the optical filter 313b, said autofluorescent-light image Zj is focused by the fluorescent-light use focusing lens 315, detected by the fluorescent-light image use high-sensitivity detecting element 316 and the visible image signal from the fluorescent-light image use high-sensitivity detecting element 316 is input to the AD converting circuit 317, and after being converted to digital data, is stored in the image data memory 411.

The interimage-image computing portion 412 computes and outputs a computed value corresponding to the ratio of each pixel value of each image stored in the image data memory 411. The image comparing portion 413 compares the computed value output from the interimage-image computing portion 412 to a standard RE value that has been prerecorded in the image comparing portion 413, determines whether each pixel represents normal tissue or diseased tissue, and based on said determination, computes and forms a computed image. The standard value RE prerecorded in the image comparing portion 413 is a value computed based on the pixel data of each pixel of an autofluorescent-light image of a living-tissue subject in which the normal tissue and the diseased tissue are clearly distinguishable, and determining whether a tissue is normal or diseased is performed by comparing whether the computed value computed by the interimage-image computing portion 412 for each pixel is larger or smaller than that of the in relation to this standard RE value.

The computed image is displayed by the computed-image use monitor 602. For cases in which the computed value is less than the standard RE value, and for .cases in which the computed value is larger than the standard RE value, by changing the display color of the zone of which a measurement has been taken, the operator can confirm the comparison result in an instant.

Note that, although two-value determination is carried out herein, the image comparing portion 413 can be eliminated, and the computed value computed by the interimage-image computing portion 412 can be left as an analog quantity and displayed, etc. The displaying of a normal image is the same as in the embodiment described above.

Note that the emission of the white light and the stimulating light and the exposure and readout by each detecting element for the normal image and the fluorescent-light image are performed according to the timing chart shown in FIG. 16. The white light and the stimulating light are controlled at respective different timings, and because they are emitted at a timing of each $\frac{1}{60}$ sec in which a 1 comma portion of an image is obtained so that they do not interfere with each other, measurement is not obstructed due to the irradiation of the other type of light.

Figure 17:
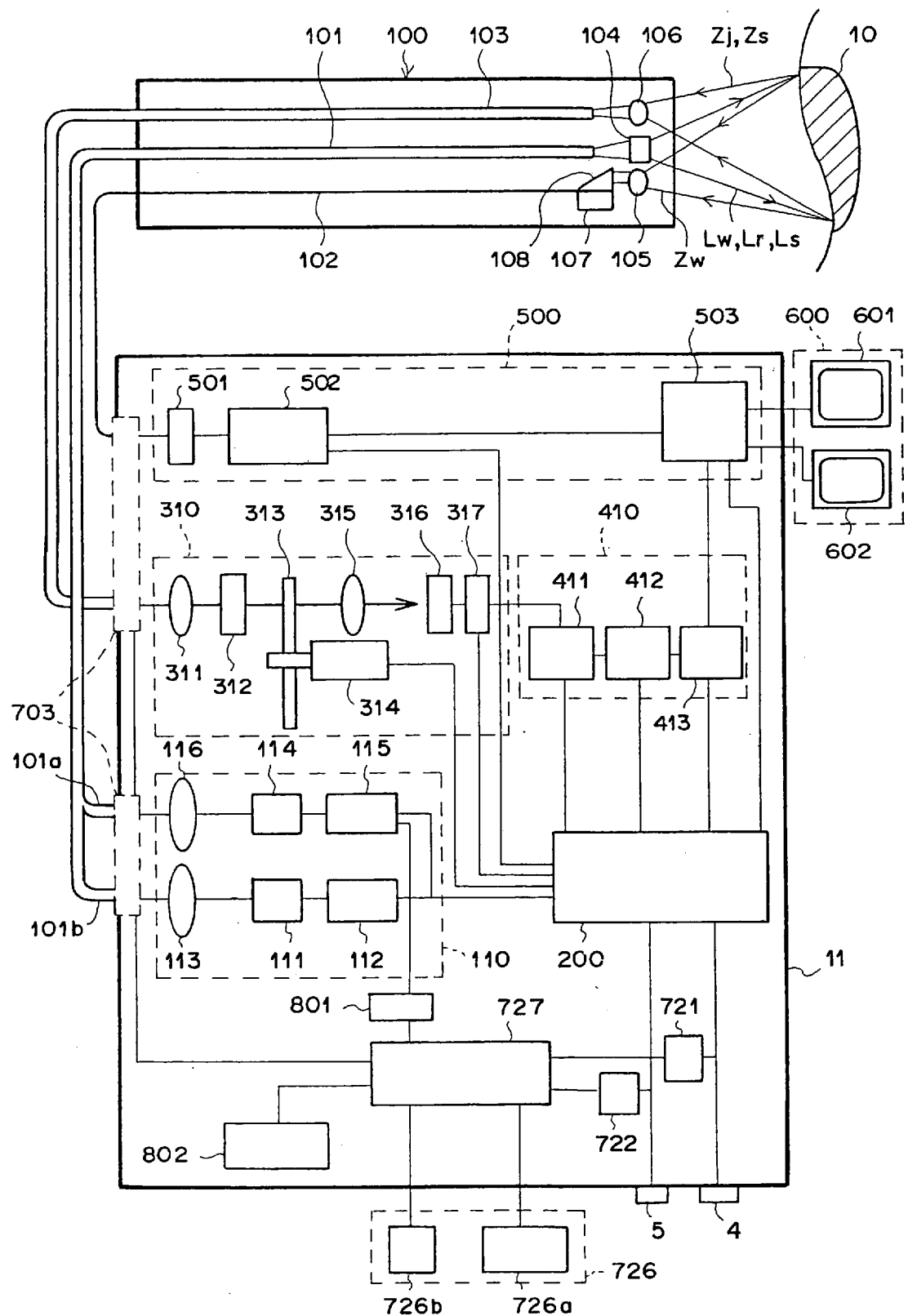
FIG. 17 is a schematic drawing of a fluorescent endoscope apparatus according to the fourteenth embodiment of the present invention.
Figure 18:
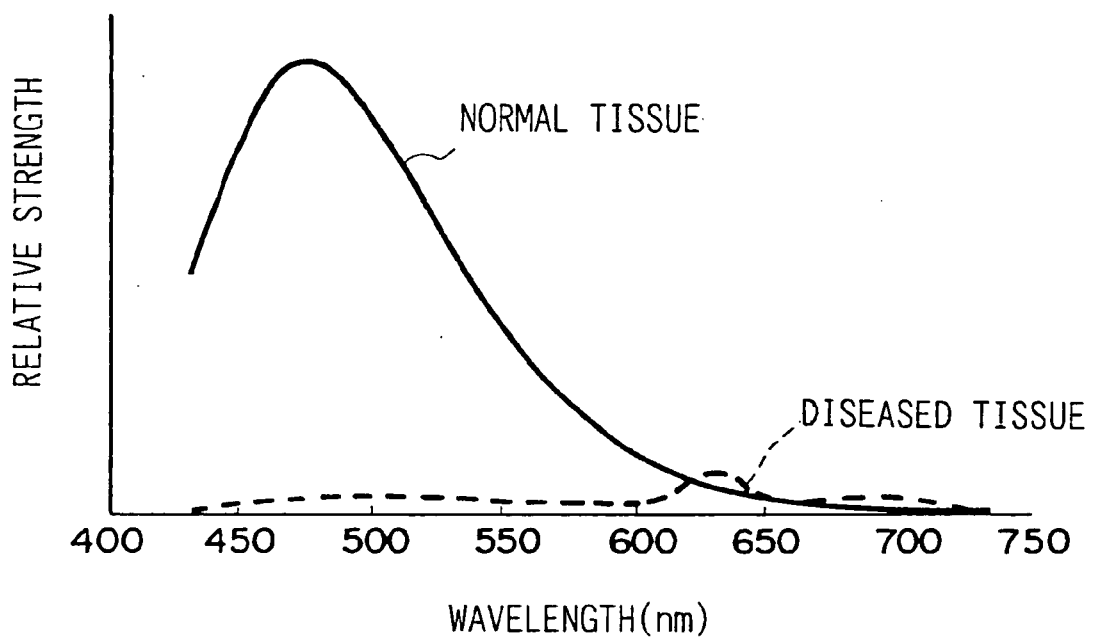
FIG. 18 is a drawing provided for explanation of the comparative distribution strengths of the fluorescent spectra of normal tissue and diseased tissue.

Next, the fluorescent endoscope apparatus according fourteenth embodiment of the present invention will be explained. FIGS. 14 and 17 are schematic drawings of the configuration of a fluorescent endoscope apparatus according to the fourteenth embodiment of the present invention. Note that in so far as further explanation of the same elements occurring in the first embodiment is not particularly required, it has been omitted.

Because the configuration of the fluorescent endoscope apparatus according to the fourteenth embodiment is substantially the same as that of the thirteenth embodiment, only elements differing will be explained. Note that in so far as further explanation of the same elements occurring in the thirteenth embodiment is not particularly required, it has been omitted.

The fluorescent endoscope apparatus according to the current embodiment comprises a stimulating-light use power source controlling means 801 for controlling the semiconductor-laser use power source 112, and a stimulating light emission prevention control data recording means 802 for recording control data for operating the stimulating-light use power source controlling means 801, and excludes the stimulating-light cutoff means 724 of the stimulating light control unit 720 of the thirteenth embodiment described above.

Next, the operation of the fluorescent endoscope apparatus of the configuration described above according to the current embodiment will be explained.

First, when the fluorescent endoscope is turned on, the power-source state detecting means 721 detects that the power source has been switched from the off to the on position, and data indicative thereof is sent to the stimulating light emission prevention control portion 727. The stimulating light emission prevention control portion 727 reads in the control data of the stimulating light emission prevention control data recording means 802 and activates the stimulating-light standby means 801, and by maintaining the semiconductor-laser use power source 112 in the standby state, the stimulating light is put in the emission-prohibited state. Further, when the system is reset, that the system has been reset is detected by the reset detecting portion 722, and data indicative thereof is sent to the stimulating light emission prevention control portion 727. After this, the stimulating light is put in the emission-prohibited state by the same operation as for when the system in turned on.

Next, the operation for when an operation to take a measurement is initiated will be explained. When an operation to take a measurement is initiated, if the patient data is entered into the input portion the input operation is detected, and by the display of a normal image, the endoscope insertion portion is inserted into the opening of a body orifice of the patient. After confirming the normal image of the section of which a measurement is to be taken, by depressing the foot witch 726b, the stimulating light emission prevention control portion 727 activates the stimulating-light standby means 801, said standby state of the semiconductor- laser use power source 112 is unlocked by the stimulating-light standby means 801, whereby the stimulating light is put in the emission-capable state, and it becomes possible to take a measurement.

Next, the operation for when successive measurements are to be taken of different patients will be explained. When a measurement is to be taken of a different patient, in order to replace or clean the endoscope, insertion portion 100, it is mandatory that the endoscope portion be removed from the image processing portion 9. Accordingly, when the endoscope insertion portion is removed from the image processing portion 9, that the endoscope insertion portion has been removed is detected by the connection detecting portion 723, and data indicative thereof is sent to the stimulating light emission prevention control portion 727. After this, the stimulating light is put in the emission-prohibited state in the same way as in the operation for when the system is turned on or reset, and also, by performing the same unlocking operation, taking a measurement again becomes possible.

Next the operation for when maintenance is to be initiated will be explained. When maintenance is initiated, in the same way as for when operations to take a measurement are initiated, the patient data is input to the input portion and the input operation is detected. However, the patient data entered at this time is pseudo patient data. Then, by the display of a normal image, the endoscope insertion portion is inserted into a body orifice of the patient. After confirming the normal image of the target tissue, by depressing the foot switch 726b, the stimulating light emission prevention control portion 727 activates the stimulating-light standby means 801, said standby state of the semiconductor-laser use power source 112 is unlocked by the stimulating-light standby means 801, whereby the stimulating light is put in the emission-capable state, whereby it becomes possible to perform maintenance operations requiring the emission of stimulating light. Also, the other operations are the same as those of the first embodiment.

According to each of the embodiments described above, the unlocking of the emission-prohibited state of the stimulating light is performed by the detection by the input operation detection portion 726a of the input operation of inputting the patient data or pseudo patient data and the detection of the switch input operation performed by the depressing of the foot pedal 726b, however, if these were to be the actual operations required before taking a measurement or performing maintenance, either one of these operations, or the combination of these operations will suffice.

In addition, the comparison by the image comparing portion 413 is not limited to being performed for each pixel position, but comparison processing can be performed for the pixel units corresponding to the binning processing of fluorescent-image use high sensitivity detecting element 316, or an operator can use a calculator and perform the comparison processing on a desired vertical by horizontal n×m pixel unit. Alternatively, the comparison processing can be performed on only an area specified by an operator, or taking into consideration the amount of calculation required to be made, an adequate number of pixels can be selected on which the comparison processing is to be performed.

Further, when there are zones for which comparison processing has not been performed, by displaying those zones in a predetermined display color, the zones that have been subjected to comparison processing can be precisely displayed. For cases in which, e.g., the comparison processing has been performed on selected pixels, an interpolated display can be performed by the comparison result of the adjacent pixels.

Still further, regarding the method of displaying a computed image, although the normal image monitor 601 and the computed image monitor 602 are of separate types in the above embodiments, a single monitor capable of displaying both types of image can also be used. Here, a method of switching between a normal image and an autofluorescent-light image can be performed automatically in a time sequence manner by use of the control-use computer 200, or an operator can use an appropriate switching means and switch the images at will. Further, a normal image and an autofluorescent-light image can be superposed and displayed. In addition, the fluorescent-image use high sensitivity detecting element 316 has been provided within the image signal processing portion 9, however, it can also be provided at the forward end portion of the endoscope insertion portion 100. However, in this case, the fluorescent-image use high sensitivity detecting element 316 disposed in the forward end portion of the endoscope insertion portion 100 can be provided with a mosaic filter, on the front face thereof, having the same functionality as the optical transmitting filter 313.

Further, any stimulating-light source emitting light having a wavelength of 400 nm to 420 nm can be selected.

What is claimed is:

1. A fluorescent endoscope apparatus comprising a projecting means for emitting stimulating light and illuminating light, an endoscope insertion portion for insertion into the body of a patient, a light guiding means provided within said endoscope insertion portion for guiding the stimulating light and illuminating light emitted from the projecting means to the section of which a measurement is to be taken, and a detecting means for detecting a fluorescent image formed of the fluorescent light emitted from the section of which a measurement is to be taken upon irradiation thereof by stimulating light guided through the guiding means and a normal image of the light reflected from the section of which a measurement is to be taken upon irradiation thereof by the illuminating light guided through the guiding means, further comprising a stimulating light emission preventing means for preventing the emission of the stimulating light, a detecting means for detecting that a forward end portion of the insertion portion is outside of the body of the patient, and a stimulating light emission prevention controlling means for preventing, via the stimulating light emission preventing means, the emission of stimulating light, based on a signal detected by the detecting means.

2. A fluorescent endoscope apparatus as defined in claim 1, wherein said detecting means is provided with a flicker detecting means for detecting the flicker appearing due to the light illuminating the inside of the diagnosis room, which is different from the stimulating light emitted by the projecting means, and a stimulating light emission prevention controlling means for preventing, via the stimulating light emission preventing means, the emission of stimulating light, based on the detection signal detected by said flicker detecting means.

3. A fluorescent endoscope apparatus as defined in claim 1, wherein said detecting means is provided with a brightness distribution detecting means for detecting the difference between the brightness distribution of the normal image and the brightness distribution occurring within the body of a patient, and a stimulating light emission prevention controlling means for preventing, via the stimulating light emission preventing means, the emission of stimulating light, based on the detection signal detected by the brightness distribution detecting means.

4. A fluorescent endoscope apparatus as defined in claim 1, wherein said detecting means is provided with a brightness detecting means for detecting that the brightness of the normal image differs from the brightness distribution when the forward end portion of the endoscope insertion portion is inside the body of the patient, and a stimulating light emission prevention controlling means for preventing, via the stimulating light emission preventing means, the emission of, stimulating light, based on the detection signal detected by the brightness detecting means.

5. A fluorescent endoscope apparatus as defined in claim 1, wherein said detecting means is provided with a color signal detecting means for detecting that the color signal of the normal image differs from the color signal occurring inside the body of a patient, and a stimulating light emission prevention controlling means for preventing, via the stimulating light emission preventing means, the emission of stimulating light, based on the detection signal detected by the color signal detecting means.

6. A fluorescent endoscope apparatus as defined in claim 1, wherein said detecting means is provided with a straight-line detecting means for detecting that the straight-line pattern of the normal image differs from the straight-line pattern occurring inside the body of the patient, and a stimulating light emission prevention controlling means for preventing, via the stimulating light emission preventing means, the emission of stimulating light, based on the detection signal detected by the straight-line detecting means.

7. A fluorescent endoscope apparatus as defined in claim 1, wherein said detecting means is provided with a light strength detecting means disposed in the end portion of the endoscope insertion portion for detecting that the light strength occurring near the side of the end portion of the endoscope insertion portion differs from the light strength inside the body of the patient, and a stimulating light emission prevention controlling means for preventing, via the stimulating light emission preventing means, the emission of, stimulating light, based on the detection signal detected by the light strength detecting means.

8. A fluorescent endoscope apparatus as defined in claim 1, wherein said detecting means is provided with a temperature detecting means disposed in the forward end portion of the endoscope insertion portion for detecting that the temperature occurring near the side of the forward end portion of the endoscope insertion portion differs from the temperature inside the body of a patient, and a stimulating light emission prevention controlling means for preventing, via the stimulating light emission preventing means, the emission of stimulating light, based on the detection signal detected by the temperature detecting means.

9. A fluorescent endoscope apparatus as defined in claim 1, wherein said detecting means is provided with a gas detecting means disposed in the forward end portion of the endoscope insertion portion for detecting that the gas surrounding the forward end portion of the endoscope insertion portion differs from the gas inside the body of the patient, and a stimulating light emission prevention controlling means for preventing, via the stimulating light emission preventing means, the emission of stimulating light, based on the detection signal detected by the gas detecting means.

10. A fluorescent endoscope apparatus as defined in claim 1, wherein said detecting means is provided with a magnetic field producing means, which is mounted at the opening of the body orifice into which the endoscope insertion portion of the endoscope apparatus is to be inserted, for producing a magnetic field, and a magnetic field detecting means disposed in the endoscope insertion portion for detecting said magnetic field, and a stimulating light emission prevention controlling means for preventing, via the stimulating light emission preventing means, the emission of stimulating light, based on the detection signal detected by the magnetic field detecting means.

11. A fluorescent endoscope apparatus as defined in claim 1, wherein said detecting means is provided with a light projecting means, which is mounted at the opening of the body orifice into which the endoscope insertion portion of the endoscope apparatus is to be inserted, for projecting light, and a reflected light detecting means for detecting the reflected light reflected by the endoscope insertion portion upon irradiation thereof by the projected light, and a stimulating light emission prevention controlling means for preventing, via the stimulating light emission preventing means, the emission of stimulating light, based on the detection signal detected by the reflected light detecting means.

12. A fluorescent endoscope apparatus as defined in claim 1, wherein said detecting means is provided with a light projecting means, which is mounted at the opening of the body orifice into which the endoscope insertion portion of the endoscope apparatus is to be inserted, fortprojecting light, and a transmitted-light detecting means disposed in the endoscope insertion portion means for detecting the transmitted light transmitted by the endoscope insertion portion upon irradiation thereof by the projected light, and a stimulating light emission prevention controlling means for preventing, via the stimulating light emission preventing means, the emission of stimulating light, based on the detection signal detected by the transmitted-light detecting means.

13. A fluorescent endoscope apparatus as defined in claim 1, wherein said detecting means is provided with an airspace volume detecting means for detecting the airspace volume between the body of a patient and the endoscope insertion portion of the endoscope apparatus, and a stimulating light emission prevention controlling means for preventing, via the stimulating light emission preventing means, the emission of stimulating light, based on the detection signal detected by the airspace volume detecting means.

14. A fluorescent endoscope apparatus as defined in claim 1, wherein said stimulating light emission preventing means is a stimulating light cutoff means inserted into the optical path through which the stimulating light is guided to the section of which a measurement is to be taken.

15. A fluorescent endoscope apparatus as defined in claim 1, wherein said stimulating light emission preventing means is a stimulating light standby means for controlling emission of the stimulating light by maintaining it in a standby state.

16. A fluorescent endoscope apparatus as defined in claim 1, wherein said stimulating light is light produced by a GaN type laser.

17. A fluorescent endoscope apparatus comprising a stimulating light emitting means for emitting stimulating light, and a stimulating light guiding means for guiding stimulating light from the projecting means to the section of which a measurement is to be taken, and an illuminating light emitting means for emitting illuminating light, and an illuminating light guiding means for guiding illuminating light from the projecting means to the section of which a measurement is to be taken, and a detecting means for detecting a fluorescent image of the fluorescent light emitted from the section of which a measurement is to be taken upon irradiation thereof by stimulating light guided through the guiding means and a normal image of the light reflected from the section of which a measurement is to be taken upon irradiation thereof by the illuminating light, and a stimulating light controlling means for controlling the emission of stimulating light from the stimulating light projecting means, further comprising a power-source state detecting means for detecting that the power source of the fluorescent endoscope apparatus has been switched from the OFF to the ON state, and a stimulating light emission preventing means for putting the stimulated light in an emission-prohibited state in which emission of stimulating light is prevented, and an unlocking operation detecting means for detecting that a predetermined operation for unlocking the emission-prohibited state has been performed, and a stimulating light emission prevention controlling means for controlling the stimulating light emission preventing means so that the stimulating light is put in the emission-prohibited state when the power-source has been detected by the power-source state detecting means to have been switched from the OFF to the ON state and the emission-prohibited state is unlocked when said predetermined operation for unlocking the emission-prohibited state of the stimulating light has been detected by the unlocking operation detecting means as having been performed.

18. A fluorescent endoscope apparatus as defined in claim 17, further comprising a reset detecting means for detecting that the fluorescent endoscope apparatus has been reset, wherein when the fluorescent endoscope apparatus is detected by said reset detecting means as having been reset, the stimulating light emission prevention controlling means causes operation of the stimulating emission preventing means and the stimulating light is put in the emission-prohibited state.

19. A fluorescent endoscope apparatus as defined in claim 17, wherein the stimulating light guiding means and the illuminating light guiding means are disposed within the endoscope insertion portion, further comprising a connection detecting mean's for detecting whether or not the stimulating light guiding. means and the stimulating light projecting means are connected, whether or not the illuminating light projecting means and the illuminating light guiding means are connected and whether or not the endoscope insertion portion and the image signal processing portion are connected, wherein when said connection detecting means detects even one of the following that the stimulating light projecting means and the stimulating guiding means are not connected; that the illuminating light projecting means and the illuminating light guiding means are not connected; or that the endoscope insertion portion and the image processing portion are not connected; the stimulating light emission prevention controlling means causes operation of the stimulating light emission preventing means and the stimulating light can be put in the emission-prohibited state.

20. A fluorescent endoscope apparatus as defined in claim 17, wherein said stimulating light emission prevention controlling means is a stimulating light cutoff means inserted into the optical path through which the stimulating light is guided to the section of which a measurement is to be taken.

21. A fluorescent endoscope apparatus as defined in claim 17, wherein said stimulating light emission prevention controlling means is a stimulating light standby means for controlling emission of the stimulating light by maintaining it in a standby state.

22. A fluorescent endoscope apparatus as defined in claim 18, further comprising a stimulating light emission prevention data recording means for recording control data for operating the stimulating light emission preventing means, wherein when the power-source state detecting means detects that the power source has been switched from OFF to ON, or when the reset detecting means detects that the stimulating light emission prevention controlling means has been reset, the stimulating light emission prevention controlling means reads said control data recorded in the stimulating light emission prevention control data recording means, and controls the stimulating light emission preventing means so that the stimulating light can be put in the emission-prohibited state.

23. A fluorescent endoscope apparatus as defined in claim 17, wherein said predetermined operation for unlocking the emission-prohibited state of the stimulating light is a manually performed operation.

24. A fluorescent endoscope apparatus as defined in claim 23, wherein said manually performed operation is an operation of inputting the patient data.

25. A fluorescent endoscope apparatus as defined in claim 17, wherein light produced by a GaN type laser is used as the stimulating light.

* * * * *